(12) United States Patent
Macfarlane et al.

(10) Patent No.: US 7,320,893 B2
(45) Date of Patent: *Jan. 22, 2008

(54) LIPOPROTEIN FINGERPRINTING METHODS USING METAL ION CHELATE SALTS

(75) Inventors: Ronald D Macfarlane, Temple, TX (US); Brian D Hosken, Bryan, TX (US); Zachlyn N Farwig, College Station, TX (US); Irma L Espinosa, College Station, TX (US); Christine L Myers, Bryan, TX (US); Steven L Cockrill, College Station, TX (US)

(73) Assignee: The Texas A&M University System, College Station, TX (US)

( * ) Notice: Subject to any disclaimer, the term of this patent is extended or adjusted under 35 U.S.C. 154(b) by 544 days.

This patent is subject to a terminal disclaimer.

(21) Appl. No.: 10/795,237

(22) Filed: Mar. 8, 2004

(65) Prior Publication Data

US 2004/0171078 A1    Sep. 2, 2004

Related U.S. Application Data

(63) Continuation of application No. 10/262,163, filed on Oct. 1, 2002, now Pat. No. 6,753,185.

(60) Provisional application No. 60/326,236, filed on Oct. 1, 2001.

(51) Int. Cl.
*G01N 33/92* (2006.01)

(52) U.S. Cl. .................. 436/71; 436/512; 436/536; 436/538; 436/539; 435/7.1

(58) Field of Classification Search .................. None
See application file for complete search history.

(56) References Cited

U.S. PATENT DOCUMENTS 4,746,605 A * 5/1988 Kerscher et al. ............. 435/7.1
5,403,745 A * 4/1995 Ollington et al. ............ 435/11

OTHER PUBLICATIONS

Macfarlane, R.D. et al. "Development of a lipoprotein profile using capillary electrophoresis and mass spectrometry", Electrophoresis, 1997, v. 18, pp. 1796-1806.*
Macfarlane et al. "Treatment of hyperlipidaemic post-menopausal women" AACC Lipids and Lipoproteins Division Newsletter, Fall 2000, vol. 14, No. 4.*

* cited by examiner

*Primary Examiner*—Yelena G. Gakh
(74) *Attorney, Agent, or Firm*—Howrey LLP

(57) ABSTRACT

Methods are disclosed which separate and identify lipoproteins in biological samples. An ultracentrifuge density gradient is used to separate lipoprotein fractions. The fractions are visualized, resulting in a lipoprotein profile. The fractions can be further analyzed by a wide array of laboratory and clinical methods. The lipoprotein profile can be used in clinical diagnoses and other medical applications.

33 Claims, 23 Drawing Sheets

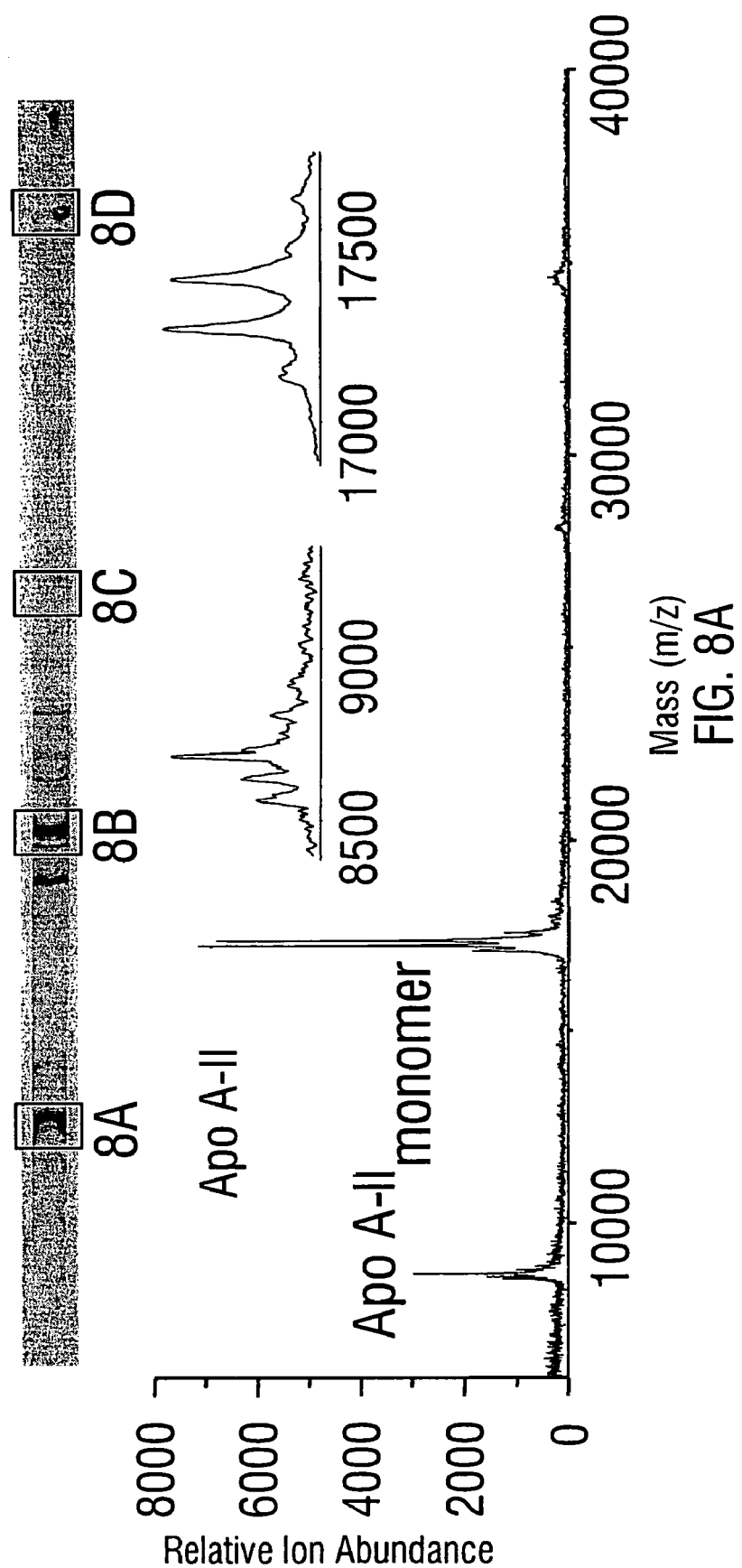

LIPOPROTEIN FINGERPRINTING METHODS USING METAL ION CHELATE SALTS

CROSS REFERENCE TO RELATED APPLICATIONS

The present application is a continuation of U.S. patent application Ser. No. 10/262,163, filed Oct. 1, 2002 and issued as U.S. Pat. No. 6,753,185, which is a non-provisional application of U.S. Provisional Patent Application Ser. No. 60/326,236 filed Oct. 1, 2001, the contents of which parent applications are incorporated herein by reference in their entirety.

FIELD OF THE INVENTION

The invention relates to methods for the analysis and quantification of lipoproteins and, more specifically, to the analysis and quantification of lipoproteins present in biological and clinical samples. In particular, a protocol is disclosed for the multi-dimensional analysis using an absolute equilibrium particle density scale.

BACKGROUND OF THE INVENTION

Lipoproteins have been identified as potential markers for cardiovascular disease risks. For example, the development of artherosclerosis is linked to a dysfunction in lipid metabolism. Cholesterol content and the distribution of cholesterol between high density lipoproteins and low density lipoproteins comprise parameters to determine a "cardiac risk profile" for coronary heart disease. Several classes of lipoproteins have been identified: very-low-density lipoproteins (VLDL), low-density lipoproteins (LDL), and high-density lipoproteins (HDL).

Separation of lipoprotein a, lipoprotein a (reduced species), and apolipoprotein a (apo(a)) using capillary zone electrophoresis has been reported (Hu, A. Z. et al., *J. Chromatog. A*, 717: 33-39, 1995). Sodium borate buffers containing SDS and acetonitrile were used. The method was reported to be advantageous over ELISA and SDS-PAGE assays due to its speed and sensitivity.

A method for profiling plasma lipoproteins based on differences in surface chemical properties was reported using HPCE (Cruzado, I. D. et al., *J. Cap. Elec.* 3(1): 25-29, 1996). Sodium dodecyl sulfate and acetonitrile were used to separate HDL and LDL particles.

High performance capillary electrophoresis was shown to separate LDL, HDL, lipoprotein a (Lp(a)) and Lp(a-) reduction products (Hu, A. Z. et al., *Am. Lab.* 28: 18N-18R, 1996). Benzyl alcohol was used to increase the UV signal intensity of highly hydrophobic lipoproteins.

A combination of capillary electrophoresis and electrospray ionization mass spectrometry was used to prepare a lipoprotein profile and cardiac risk profile analysis (Macfarlane, R. D. et al., *Electrophoresis* 18: 1796-1806, 1997). Ultracentrifugation and image analysis was used to separate the VLDL, LDL, and HDL fractions. Each of the individual fractions was further analyzed using capillary electrophoresis. Mass spectrometry was used to determine the isoform distribution for apoproteins. Lipid profile analyses were performed on nearly 100 clinical samples. Abnormalities in the lipid profiles were observed with samples from every cardiac patient. The analyses were also used to monitor the effects of a statin drug on a hypertriglyceridemic patient.

Capillary electrophoresis was reported as being useful for the characterization and quantitation of apolipoprotein B-100 (Cruzado, I. D. et al., *J Lipid Res.*, 39: 205-217, 1998). Sucrose gradient ultracentrifugation and capillary electrophoresis were used to analyze serum. The described method was suggested to have the potential for high accuracy due to the elimination of various systematic errors associated with previously used methods.

The use of capillary electrophoresis was suggested as having potential for higher resolution, greater specificity, speed, and automation for detection and quantitation of lipoproteins than other existing methods (Watkins, L. K. et al., *Methods in Molecular Medicine, vol. 27: Clinical Applications of Capillary Electrophoresis*, Ed. Stephen M. Palfrey, pages 99-108, 1999). Samples were separated into lipoprotein classes by ultracentrifugation, and the protein fractions measured by capillary electrophoresis.

Macfarlane and McNeal described the concept of a lipoprotein fingerprint in "What is your Lipoprotein Fingerprint?" (AACC Lipids and Lipoproteins Division Newsletter, vol. 14, no. 4, Fall 2000). The profile involves measurement of the lipoprotein particle density profile of VLDL, LDL, and HDL. The lipoprotein fingerprint measured was a composite of five profiles. Sections of the separated material were obtained and analyzed by capillary zone electrophoresis to identify sub-fractions. MALDI analysis was used to identify small proteins sequestered within the lipoprotein particles.

U.S. Pat. No. 5,783,400 describes a method for the isolation of lipoprotein and subsequent quantification of its mass and cholesterol content. Biological fluids are fractionated using an ultra-centrifuge. The fraction is reacted with immobilized ligand to remove non-Lp(a) substances. Protein concentration, protein isoform determination, and cholesterol content can be obtained from the fractionated material.

U.S. Pat. No. 6,090,921 offers a process for purifying apolipoprotein A or apolipoprotein E from human plasma. Plasma is mixed with polyethylene glycol to precipitate impurities, and the Apo A or Apo E purified by anion-exchange chromatography and gel filtration.

Despite advances made to date, there exists a need for rapid, accurate, and reproducible assays for the separation and identification, and quantitation of lipoproteins.

SUMMARY OF THE INVENTION

Lipoprotein profiles are prepared via an absolute thermodynamic equilibrium density scale using an ultracentrifuge. The use of standards is not required. The lipoprotein subclasses can be identified by their location in the equilibrium density gradient. Individual subclasses can readily be isolated by freezing, cutting, and thawing the centrifuge sample. The presence or absence of a metabolic condition or disease can be correlated by the concentration of one or more lipoprotein subclasses.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

| FIG. | Description |
|---|---|
| 1 | Correlation of position in centrifuge tube and lipoprotein fractions (Normal profile) |
| 2 | Correlation of position in centrifuge tube and lipoprotein fractions (Identification of risk factors in the lipoprotein density profiling method).

DETAILED DESCRIPTION OF THE INVENTION

Figure 1:
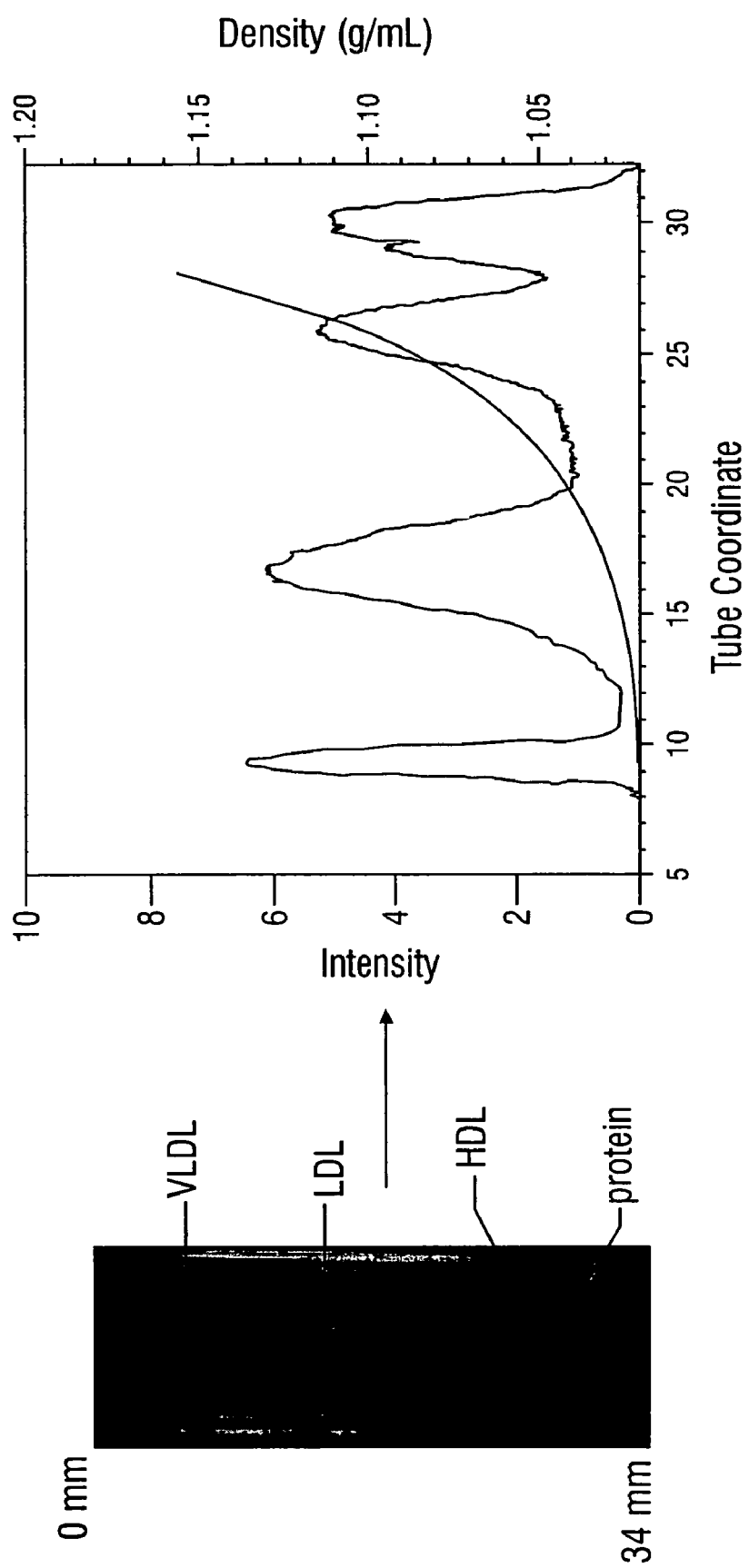
Figure 2A:
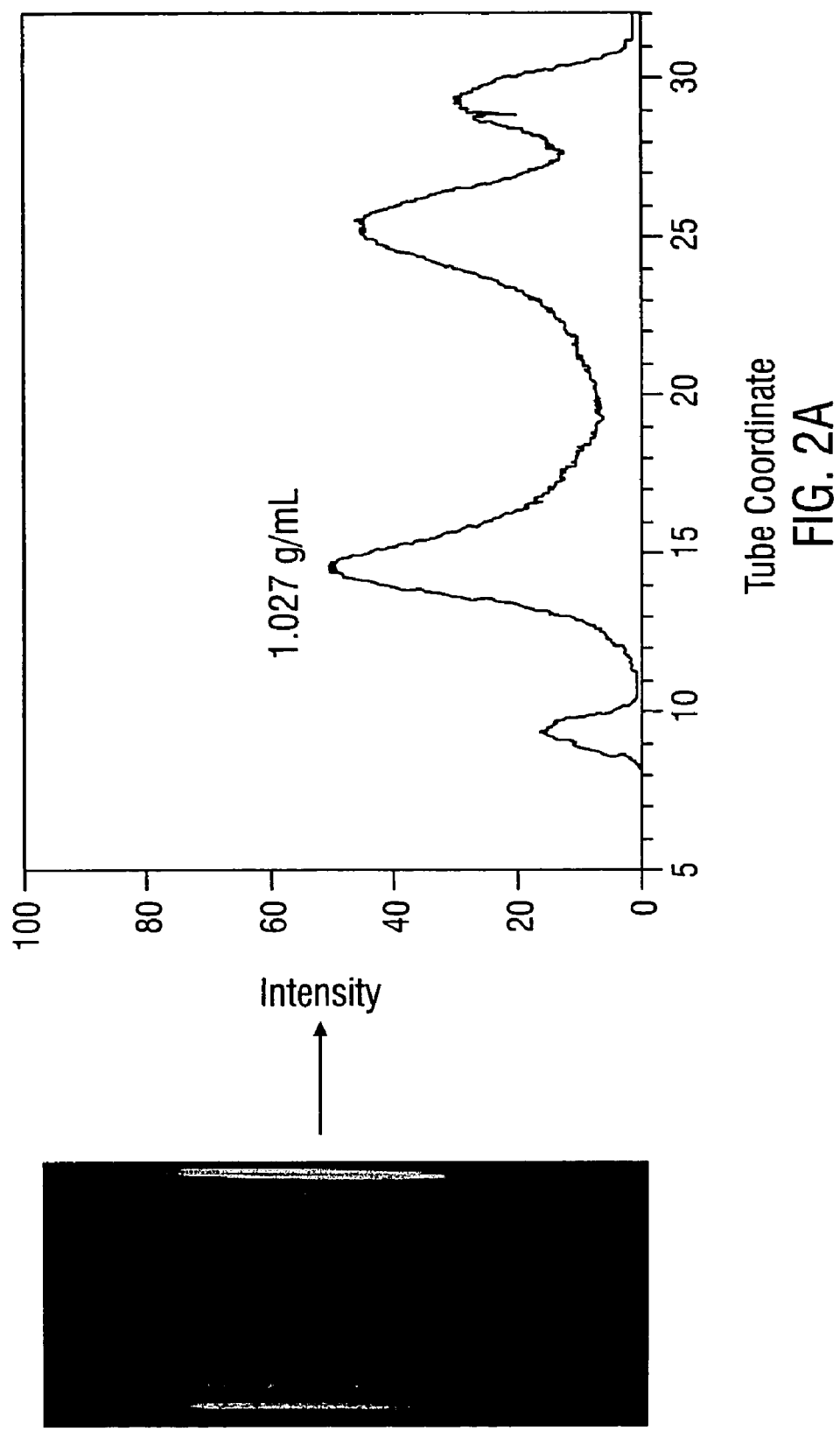
FIG. 2A is buoyant LDL.
Figure 2B:
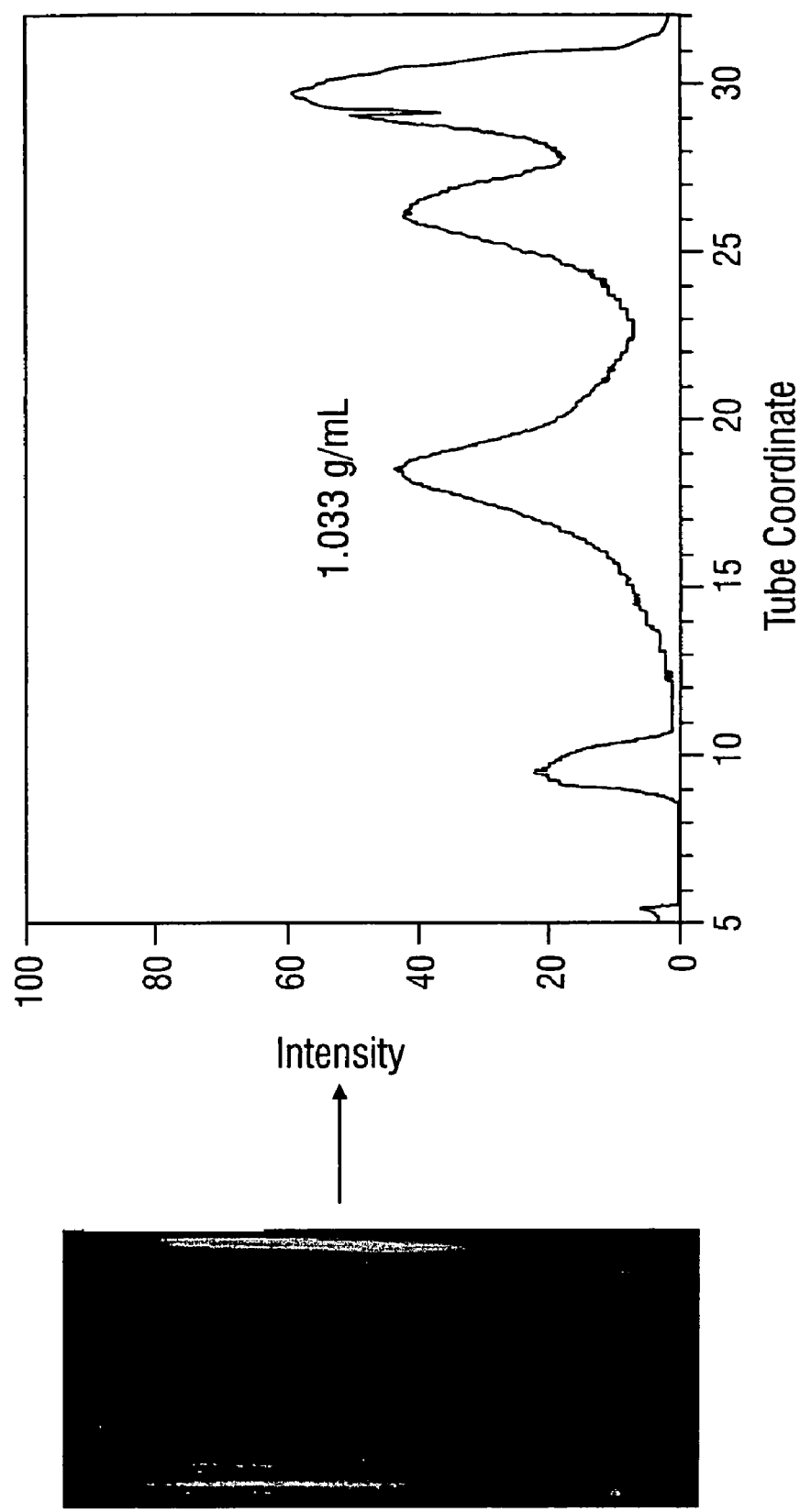
FIG. 2B is dense LDL.
Figure 2C:
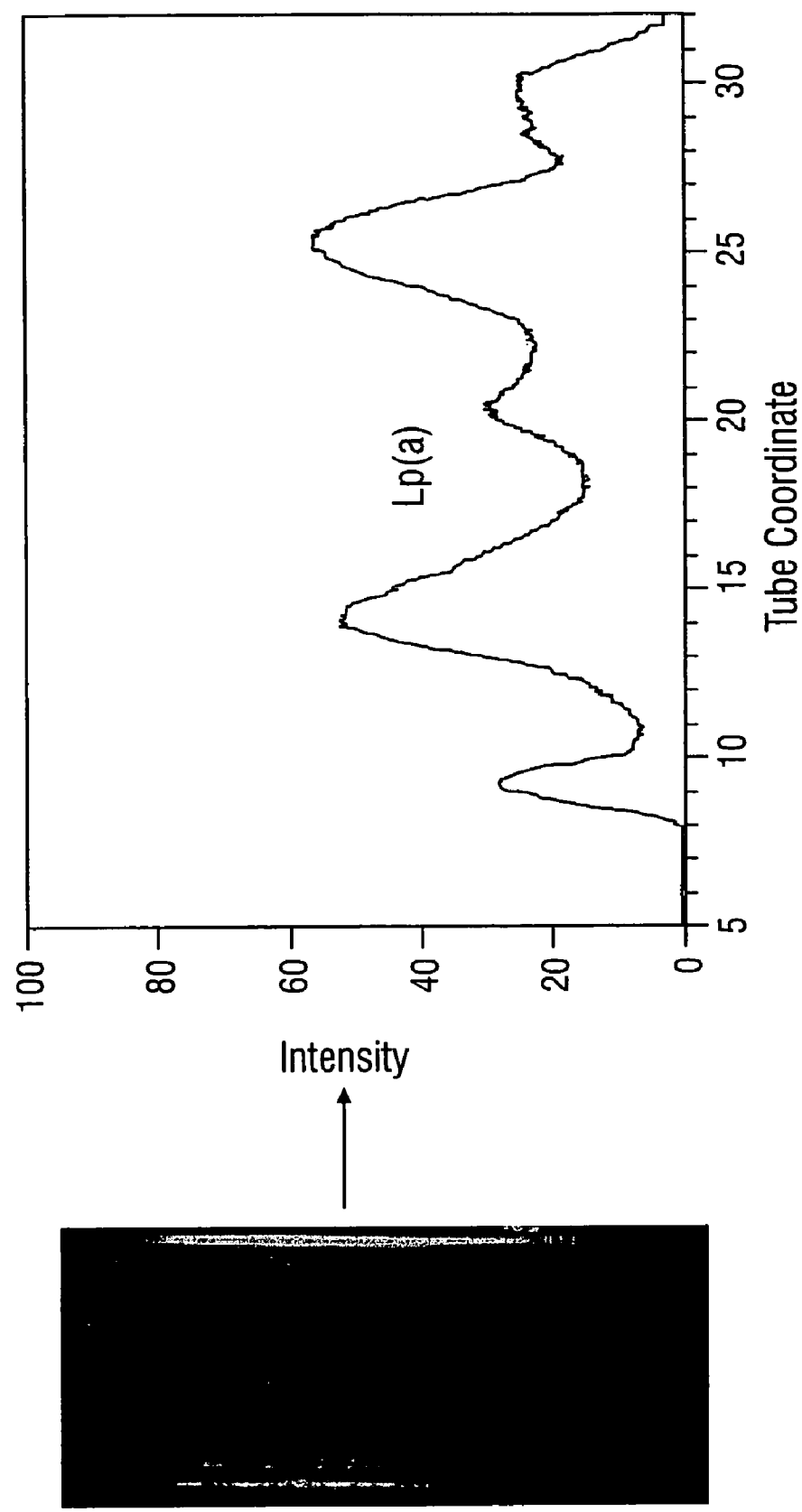
FIG. 2C is Lp(a)
Figure 2D:
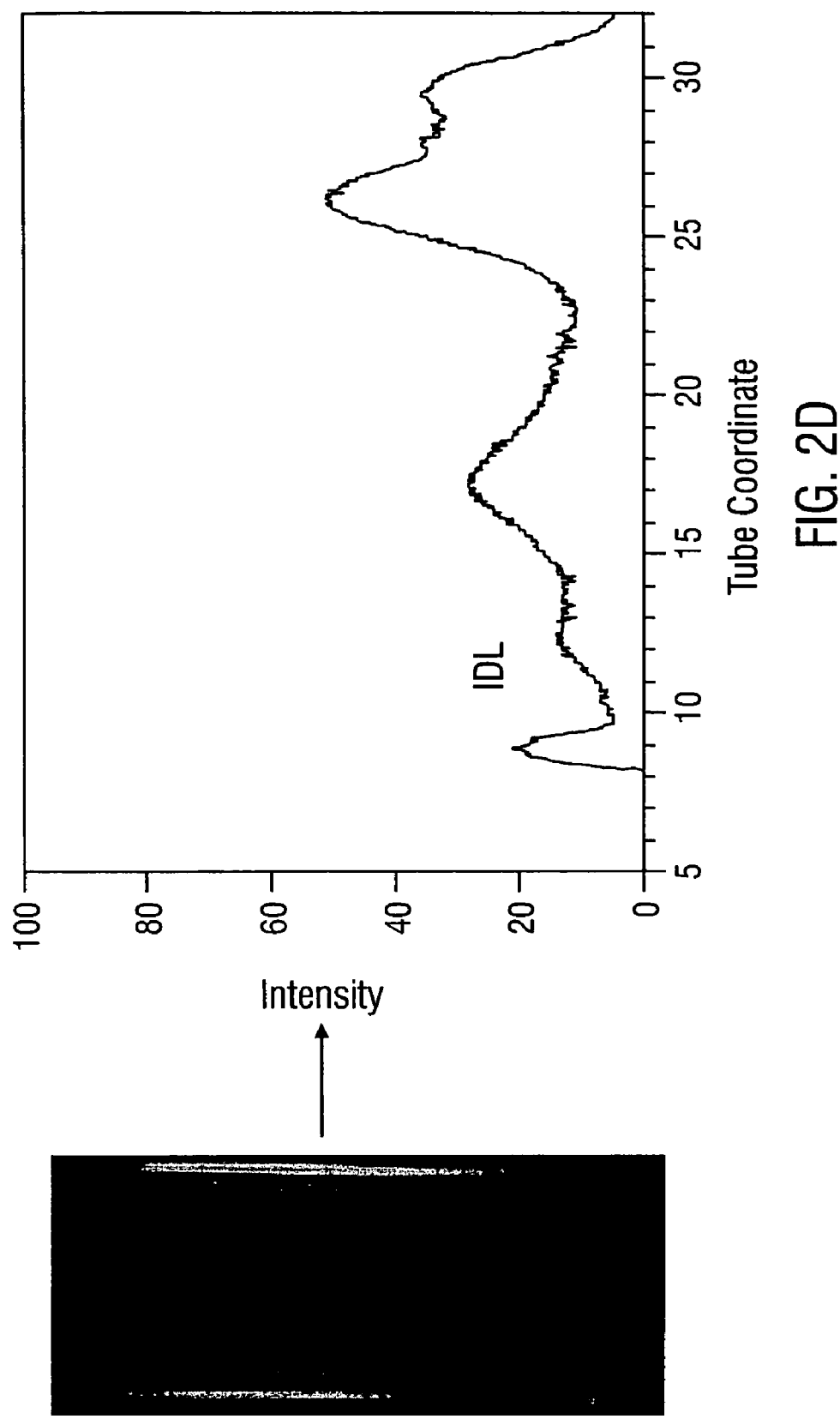
FIG. 2D is remnant VLDL. |
| 3 | Concentration curves for LDL.

Serum and plasma can be obtained from blood by methods well known to those of skill in the art. For example, blood can be clotted, and the serum or plasma isolated by low speed centrifugation. Serum and plasma can be stained by a dye such as NBD $C_6$-ceramide or Sudan Black B, and subjected to ultracentrifugation. The visualization dye is chosen to interact with the surface of the lipoproteins and has saturation kinetics so that the uptake is proportional to particle concentration. The dye can be a visible dye or a fluorescent dye.

The stained plasma or serum is added to the density gradient forming solute solution, forming a uniform solution. The CsBiEDTA solute system, sucrose, or other gradient forming agents can be used. This use of a homogeneous starting solution is both simple and convenient.

A density gradient can be formed by a method comprising providing a solution of one or more metal ion chelate complexes and applying a centrifugal field to the solution until a density gradient is formed. The properties of the density gradient are a function of the particular metal ion chelate complex, the concentration of the solution, temperature and the magnitude of the centrifugal field.

As used herein, the term "metal ion chelate complex" refers to a complex formed between a metal ion and a chelating agent. The metal ion can generally be any metal ion. Metal ions of the present invention include, but are not limited to ions of copper, iron, bismuth, zinc, cadmium, calcium, thorium and manganese. Presently preferred metal ions are ions of copper, iron, calcium, thorium and bismuth.

One of skill in the art would recognize the term "chelating agent" to refer to a particular type of ligand that can form a complex with a metal ion, wherein the ligand comprises more than one atom having unshared pairs of electrons that form bonds or associations with the same metal ion. Chelating agents are also referred to as polydentate ligands. Examples of chelating agents according to the present invention include, but are not limited to oxalate, ethylenediamine, diethlyenetriamine, 1,3,5-triaminocyclohexane and ethylenediaminetetraacetic acid (EDTA). EDTA is capable of donating up to six unshared pairs of electrons to the metal chelate complex and is a presently preferred chelating agent.

Metal ion chelate complexes may sometimes require one or more positively charged counter-ion to balance the overall charge of the complex. Examples of counter-ions include, but are not limited to lithium, sodium, potassium, cesium, magnesium, calcium and ammonium as well as counter-ions such as ammonium complexes, for example tetrabutylammonium. When more than one counter-ion is required to balance the overall charge, the counter-ions can be mixed. For example, a metal ion chelate complex requiring two positive charges can have one positive charge supplied by sodium and the other by potassium.

The properties of the density gradient can be modified by choosing different combinations of metal ions, chelating agents and counter ions. Examples of suitable metal ion chelate complexes include, but are not limited to NaCuEDTA, NaFeEDTA, NaBiEDTA and CsBiEDTA. CsBiEDTA is a presently preferred metal ion chelate complex. Solutions of more than one metal ion chelate complex can also be used to form density gradients according to the present invention.

The concentration of the metal ion chelate complex can generally be any concentration range. The concentration of the metal ion chelate complex solution is typically about 0.01 M to about 0.7 M, and more typically about 0.1 M to about 0.3 M. In general, a lower concentration results in a lower density range while a more concentrated solution typically yields a higher range of densities.

Density gradients may be disposed in any suitable container. Density gradients are typically disposed within a tube, particularly within a centrifuge tube. The centrifugal field can be applied to the solution by spinning the tube in a rotor. The spin rate affects the speed at which the density gradient is formed, a faster spin rate typically resulting in faster gradient formation. Rapid gradient formation is desirable because it reduces the time required for the separation. However, too rapid of a gradient formation may adversely affect particle separation because the particles do not have a chance to find their isopycnic point before the gradient becomes too steep.

Any of the various rotor/tube configurations know in the art can be used with the gradients of the present invention. Examples include fixed angle rotors, vertical tube rotors and swinging bucket rotors. A typical rotor configuration is a fixed angle of about 30 degrees.

The density gradients formed can be essentially exponential density gradients. That is, the density of the solution varies essentially exponentially as a function of position from one end of the tube to the other. Exponential geometry of a density gradient is an indication that the gradient is at equilibrium. This type of gradient is ideal for isopycnic mode separations wherein the particles migrate through the gradient until they reach a position that is equal to their own density. Isopycnic mode separations are desirable because they reflect the true equilibrium densities of the particles.

Density gradients are particularly suited for separating lipoproteins of differing densities from one another. Lipoproteins are typically divided into classes based on their density and compositions. Such classes include very low density lipoprotein (VLDL), low density lipoproteins (LDL), intermediate density lipoproteins (IDL), high density lipoproteins (HDL) and lipoprotein(a) (Lp(a)). The relative amounts of these lipoproteins in the plasma are important clinical diagnostic indicators for coronary heart disease.

Isopycnic mode separations are particularly suitable for the analysis of lipoproteins because the isopycnic mode yields substantial information about the equilibrium density of the lipoproteins. This information is relevant as a clinical diagnostic for coronary heart disease.

The serum, plasma, or other material is mixed with the density gradient components in a centrifuge tube or other container. The resulting solution is spun in an ultracentrifuge, and scanned in a spectrophotometer or is imaged using a digital camera (FIGS. 1 and 2). The formed density gradient is useful for separating the stained serum into its component parts.

The image is converted into a particle density profile. The location of bands within the ultracentrifuge tube is converted to the density of the band (using the refractive index, gravimetry, and uv-absorbance of the band).

Changes within the particle density profile can be used to identify the presence or absence of clinical risk factors, monitoring myocardial infarction patients, and other clinical diagnostic uses. For example, the absence of the super-dense LDL particle (d=1.040-1.045 kg/M$^3$) would indicate the possible presence of atherosclerotic lesions in the vasculature.

Particular regions of interest can be selected and isolated from the ultracentrifuge tube using a freeze, cut, and thaw method. For example, the VLDL, LDL, and HDL fractions can be isolated and analyzed for cholesterol and triglyceride levels using standard analytical assays.

One embodiment of the invention is directed towards a method of obtaining the lipoprotein profile of a sample. The method can comprise contacting a sample that contains lipoproteins, a density gradient forming agent, and a dye to produce an unseparated mixture, subjecting the unseparated mixture to a centrifuge force field under conditions suitable to produce a separated mixture, wherein the separated mixture comprises multiple lipoprotein fractions, and visualizing the multiple lipoprotein fractions to obtain a lipoprotein profile.

The sample can generally be any sample containing lipoproteins or suspected of containing lipoproteins. An example of such a sample is plasma or serum. The plasma or serum can be obtained from generally any animal, for example, humans, dogs, cats, horses, cows, sheep, goats, moose, bear, or pigs.

The density gradient forming agent can generally be any agent that forms a density gradient when exposed to a centrifuge force field. Examples of such an agent include sucrose, CsBiEDTA, NaCuEDTA, NaFeEDTA, and NaBiEDTA. Presently preferred density gradient forming agents are sucrose and CsBiEDTA.

The dye can generally be any dye. Preferably, the dye is a visible or fluorescent dye. Examples of such dyes include NBD C$_6$-ceramide (6-[N-(7-nitrobenz-2-oxa-1,3-diazole-4-yl) amino]hexanoyl-D-erythro-sphingosine; Molecular Probes, Eugene, OR, Cat. No. N-1154) and Sudan Black B. The dye can be a lipophilic or protein stain. Examples of a lipophilic and protein stain include Sudan Black B and Coomassie Brilliant Blue R. The dye can also be a fluorescent membrane probe. Examples of such probes include NBD, DiI (3,3'-dioctadecylindocarbocyanine) (D-282), DiA (N,N-dipentadecylaminostyrilpyridinium), (D-3883), BODIPY (dipyrrometheneboron difluoride) C5-HPC (D-3795).

The unseparated mixture can further comprise a buffer. Examples of buffers include phosphate, acetate, and tris.

The centrifuge force field can generally be any strength sufficient to separate the lipoprotein fractions. Preferably, the force field is at least about 400,000×g. A range of the force field strength is about 400,000×g to about 600,000×g. Specific examples of force field strength include about 400,000×g, about 450,000×g, about 500,000×g, about 550,000×g, about 600,000×g, and ranges between any two of these values.

The multiple lipoprotein fractions can generally comprise any lipoprotein fractions. Example fractions include a VLDL fraction, a IDL fraction, a LDL fraction, a Lp(a) fraction, and a HDL fraction. A separated mixture may contain one or more of these fractions, depending on the composition of the original sample.

The visualizing step can comprise photographing the separated mixture. The photograph can be digitized into a computer and analyzed. Alternatively, the separated mixture can be scanned directly into a computer. The lipoprotein profile can be quantized to afford the concentration of the individual lipoprotein fractions.

The separated mixture can be frozen and sliced to isolate the multiple lipoprotein fractions. The slices can be subsequently thawed. The freezing step preferably comprises contacting the container containing the separated mixture (i.e. the centrifuge tube) and liquid nitrogen for a sufficient period of time to freeze the separated mixture.

Figure 9:
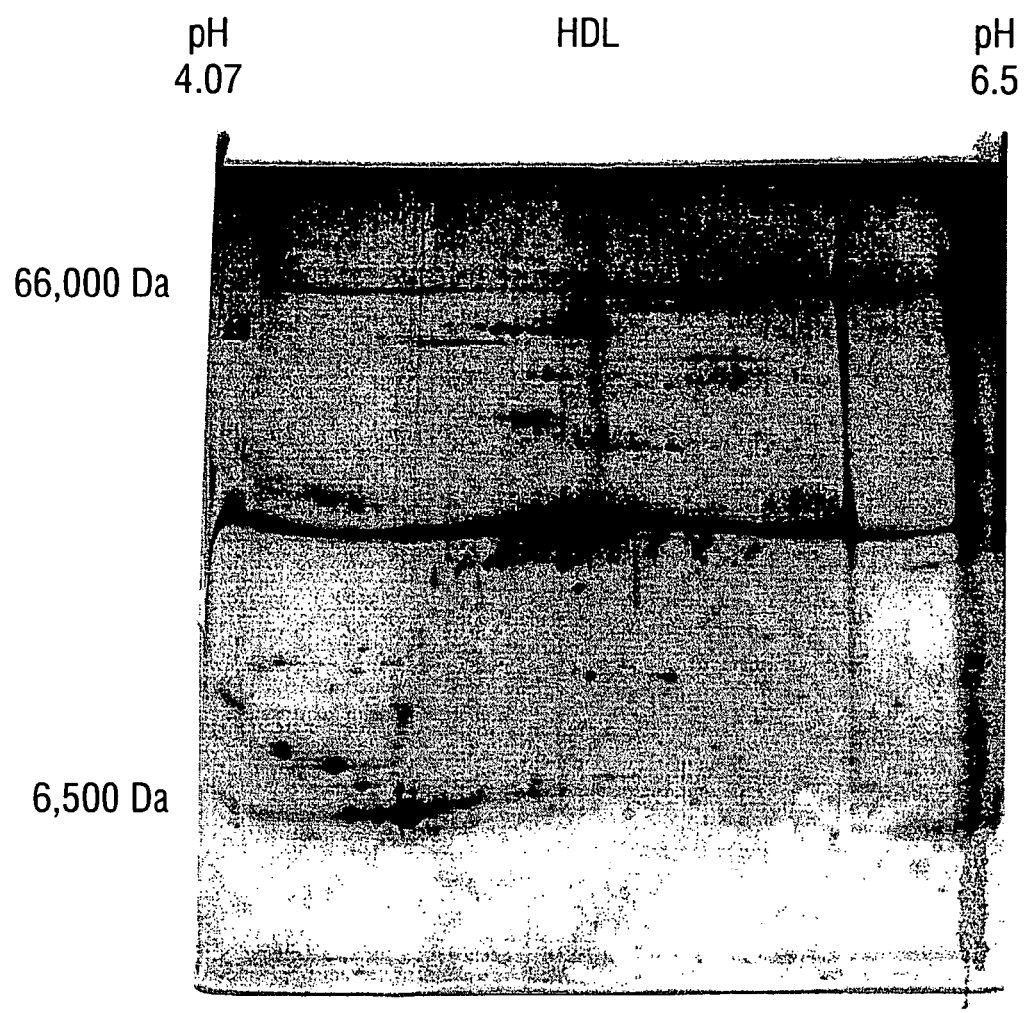
Figure 12:
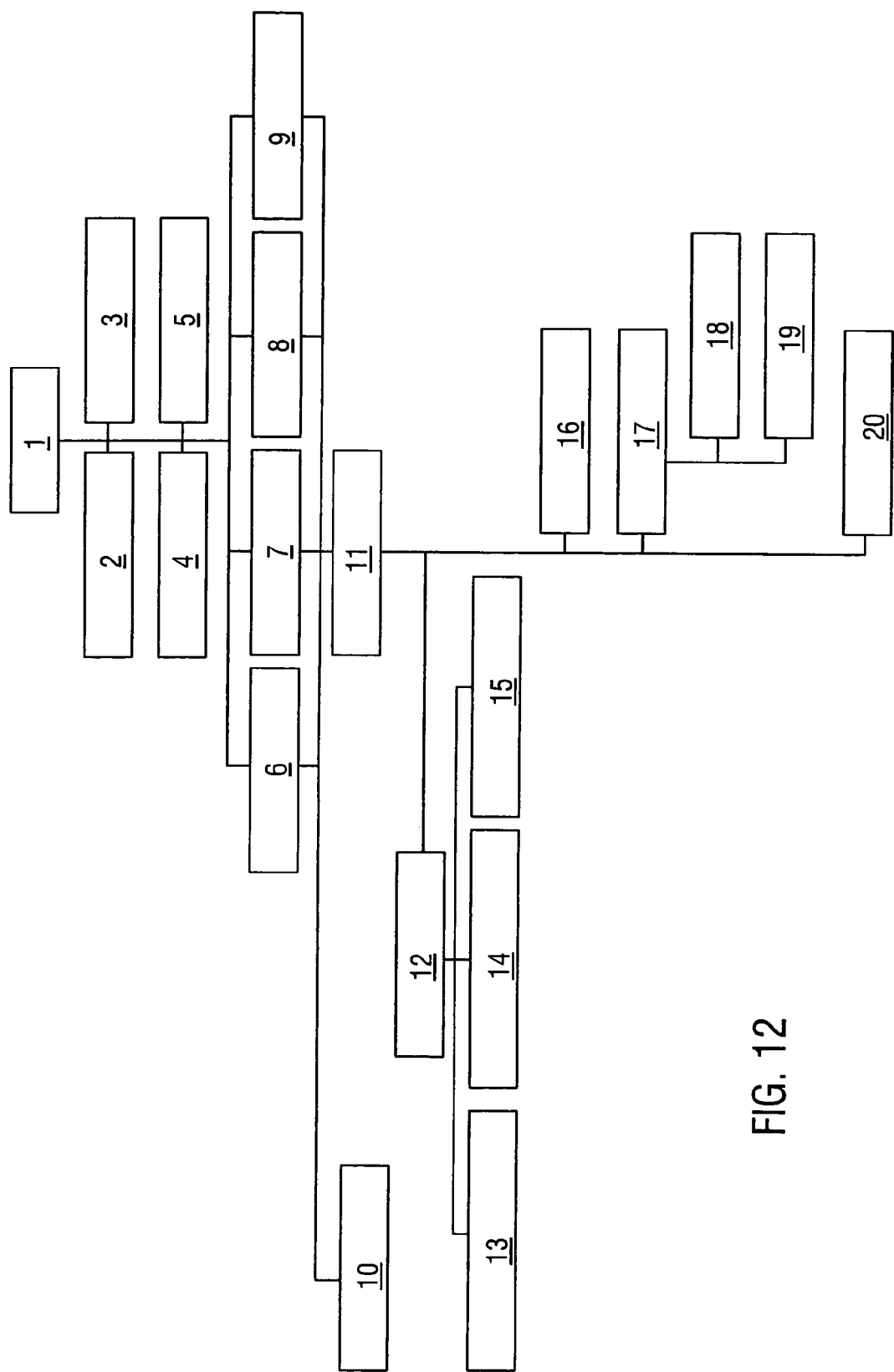

Isolated lipoprotein fractions can subsequently be analyzed by a variety of methods (FIG. 12). These methods include capillary electrophoresis (FIG. 4), solid phase extraction, mass spectrometry, thin layer chromatography, electron paramagnetic resonance (EPR), immobilized pH gradient isoelectric focusing (FIG. 7), matrix assisted laser desorption/ionization (MALDI) mass spectrometry (FIG. 5), electrospray ionization mass spectrometry (ESI-MS), and two dimensional gel electrophoresis (FIG. 9).

An alternative embodiment is directed towards methods for the separation of total lipoprotein from the other serum proteins. The serum is mixed with the density gradient solute at high density, at least about 1.3 kg/m$^3$. The resulting solution is ultracentrifuged. The lipoproteins concentrate at the top of the tube, while the serum proteins sediment at the bottom of the tube. The total lipoprotein fraction ("TLF") can be analyzed by 2D gel electrophoresis and mass spectrometry. This method can be used to identify biomarkers for predicting restenosis in coronary angioplasty (PTCA) patients.

An additional embodiment of the invention involves the use of the above described methods in monitoring the health of an animal or patient. The lipoprotein profile can be determined at one time to produce a "snapshot" of the patient's serum lipoprotein content. Additionally, the profile can be determined at multiple time points to monitor changes in the profile due to medication, exercise, changes in diet, or other changes in lifestyle.

A further embodiment of the invention is directed towards differential density profiling methods. The methods involve contacting the sample with an antibody that reacts/binds to a particular lipoprotein fraction. Removal of the lipoprotein-antibody complex affords a reduced sample that has had that particular lipoprotein fraction removed. Subtracting the lipoprotein profile of this reduced sample from the lipoprotein profile of the original sample generates a differential density profile. This differential density profile provides a distribution of the particular lipoprotein fraction in the original sample. The particular order of obtaining the two lipoprotein profiles is not critical—the original sample profile can be prepared first, second, or simultaneously with the profile of the reduced sample.

The method of obtaining a differential density profile of a sample can comprise contacting the sample, a density gradient forming agent, and a dye to produce a first unseparated mixture, wherein the sample contains lipoproteins; subjecting the first unseparated mixture to a centrifuge force field under conditions suitable to produce a first separated mixture, wherein the first separated mixture comprises a first set of multiple lipoprotein fractions; visualizing the first set of multiple lipoprotein fractions to obtain a first lipoprotein profile; contacting the sample and an antibody that binds to a lipoprotein fraction to form an antibody-lipoprotein complex; separating the antibody-lipoprotein complex from the sample to produce a reduced sample; contacting the reduced sample, a density gradient forming agent, and a dye to produce a second unseparated mixture; subjecting the second unseparated mixture to a centrifuge force field under conditions suitable to produce a second separated mixture, wherein the second separated mixture comprises a second set of multiple lipoprotein fractions; visualizing the second set of multiple lipoprotein fractions to obtain a second lipoprotein profile; and subtracting the second lipoprotein profile from the first lipoprotein profile to obtain a differential density lipoprotein profile.

The original sample can be plasma or serum. The antibody can be monoclonal or polyclonal. The antibody can be immunoreactive against any lipoprotein fraction in the original sample. Separation of the antibody-lipoprotein complex from the sample can be accomplished by generally any acceptable method. For example, the complex can be separated by immunoprecipitation, paramagnetic beads, gel filtration chromatography, or antibody capture chromatography.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Preparation and Separation of Lipoproteins with a Visible Dye

A 250 µL volume of serum was stained with 10 µL of 1% w/v Sudan Black B in dimethylsulfoxide, and allowed to incubate for 30 minutes at 37° C. An 800 µL volume of 20% sucrose was pipetted into an 11×34 mm polycarbonate open-top centrifuge tube, followed by 400 µL of dilute serum stained with Sudan Black B. The tube was centrifuged in a Beckman TL-100 ultracentrifuge equipped with a 30° fixed angle TLA 100.2 rotor at 436,000×g and 20° C. for 6 hours.

The ultracentrifuge tube was photographed, and the image was digitized with a gray-scale scanner.

Conversion of a location along the tube axis to the solution density at that point was made by measuring the shift in the image of the 160 µm diameter wire mounted in back of the centrifuge tube. Photographs were recorded for a set of ultracentrifuge tubes containing sucrose solutions with accurately known densities from 1.0000 to 1.1270 g/mL. The shift in the position of the wire due to the refractive index of the solution was measured for each density standard with a precision of ±0.025 mm. The relationship between image shift and solution density were thereby established.

Example 2

Separation of Lipoproteins Using a Fluorescent Probe

In a 1.5 mL microcentrifuge tube, 55 µL of serum was diluted with 540 µL of water and 600 µL of 20% (w/w) CsBiEDTA. A 5 µL aliquot of NBD $C_6$-Ceramide (2 mg/mL in DMSO) was added and the tube and was vortexed. The sample was incubated for 30 minutes at room temperature. A volume of 1100 µL of this sample was then transferred to the 1.5 mL centrifuge tube. Tubes were centrifuged for 4 hours and 40 minutes at 120,000 rpm and 20° C. (527,000× g). After centrifugation, 300 µL of water was layered over the gradient so that the VLDL band could be visualized without interference from the meniscus. The tubes were photographed with the following camera settings for the Nikon Coolpix 5000. In the manual focus mode, the focal distance was set at 0.26 ft and the camera lens was adjusted to its maximum magnification (3× optical). A ½ second shutter speed and F# 7.6 were selected in the manual exposure mode. The gain on the camera was set at ISO100 and the uncompressed file size (.tiff) was selected.

Example 3

Digital Analysis of Lipoprotein Profile Image

The camera image file was transferred to a computer and then analyzed with Kodak Digital Science 1D software. This software, developed for analyzing one dimensional gels, creates a lane on the image and then measures the gray scale intensity along this lane. A calculation is made to find the position in mm (tube coordinate) from a row number (FIG. 1).

Example 4

Density Determination

Density gradients were formed in a Beckman (Palo Alto, Calif.) Optima TLX ultracentrifuge, TLA 120.2 fixed angle rotor, and 1.5 mL, thick-walled, open top, polycarbonate UC tubes. Tubes containing 1100 µL of a CsBiEDTA solution were centrifuged at 20° C. Gradient shapes were determined by sampling the UC tube at different locations and then measuring the CsBiEDTA concentration using the previously determined calibration curves for concentration and density. The gradients were sampled by removing a series of 10.00±0.04 µL aliquots from the centrifuge tube with a 20 µL micropipette (model P-20, Rainin Instrument Co., Inc., Woburn, Mass.). The pipette was clamped to a ring stand that was secured to a lab jack. The lab jack was adjusted so that the tube could be sampled at different depths. The tube was sampled sequentially from the top so that the gradient below each sample was not disturbed.

The tube was photographed while the sample was being removed so that the exact location of the aliquot was known. The sample from the gradient was then diluted with 990.0±1.3 µL of water and the absorbance was measured in duplicate and averaged. The density was calculated from the absorbance calibration curve and then plotted as a function of tube coordinate measured in mm.

Example 5

Isolation of Lipoprotein Fractions

The ultracentrifuge tube was frozen in liquid nitrogen, and sliced into four sections at predetermined positions in order to recover the VLDL, LDL, HDL, and pelleted fractions that contain the more dense serum proteins. The slicing was performed using a Model 1672, 16 inches, 2-speed Dremel scroll saw. Low molecular weight compounds were removed from each fraction by ultrafiltration.

Example 6

Total Lipoprotein Fraction Analysis

A second ultracentrifuge separation using a sodium bromide gradient can be performed to recover the total lipoprotein fraction. The serum proteins penetrate the salt gradient. The tube is frozen and sliced to obtain the total lipoprotein fraction. This fraction is subjected to delipidation using a reverse-phase solid phase extraction cartridge (SPE). ApoB-100 is not recovered, as it strongly binds to the SPE cartridge. The apolipoprotein fraction can be analyzed by matrix-assisted-laser desorption ionization (MALDI) and isoelectric point profiling (pI).

MALDI can be used to identify small proteins that have been sequestered by the lipoprotein particles. These include A-, C-, and E-apolipoproteins. The pI profile identifies pI polymorphism for species with the same or nearly same molecular weight having different pI values. These profiles can be obtained using immobilized pH gradient gels (IPG).

Example 7

ApoB-100 Analysis

ApoB-100 is a key protein in LDL. Some domains are buried within the lipophilic LDL core, while others such as the ligand for the LDL receptor are exposed to the aqueous environment. Using the LDL fraction obtained from the ultracentrifuge tube, a mass spectral map of enzymatic or chemically digested fragments is obtained. This map can be used to search for mutations, post-translational modifications, and conformational differences in apoB-100 that reflect the manner in which it is bound to the LDL particle.

Example 8

Correlation with Cholesterol Levels

Figure 3A:
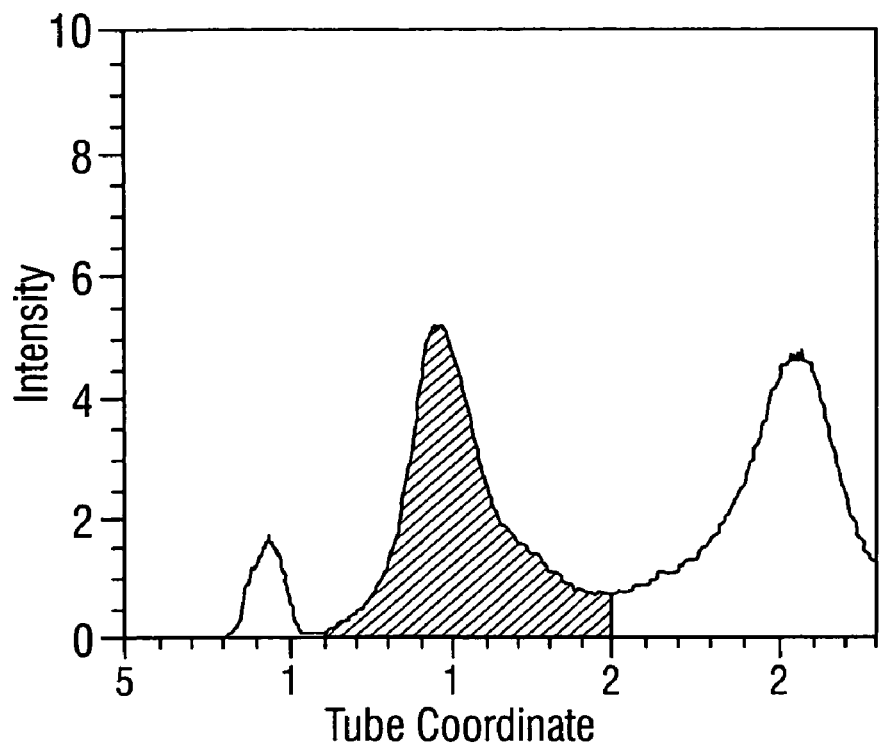
FIG. 3A is a plot of intensity against tube coordinate.
Figure 3B:
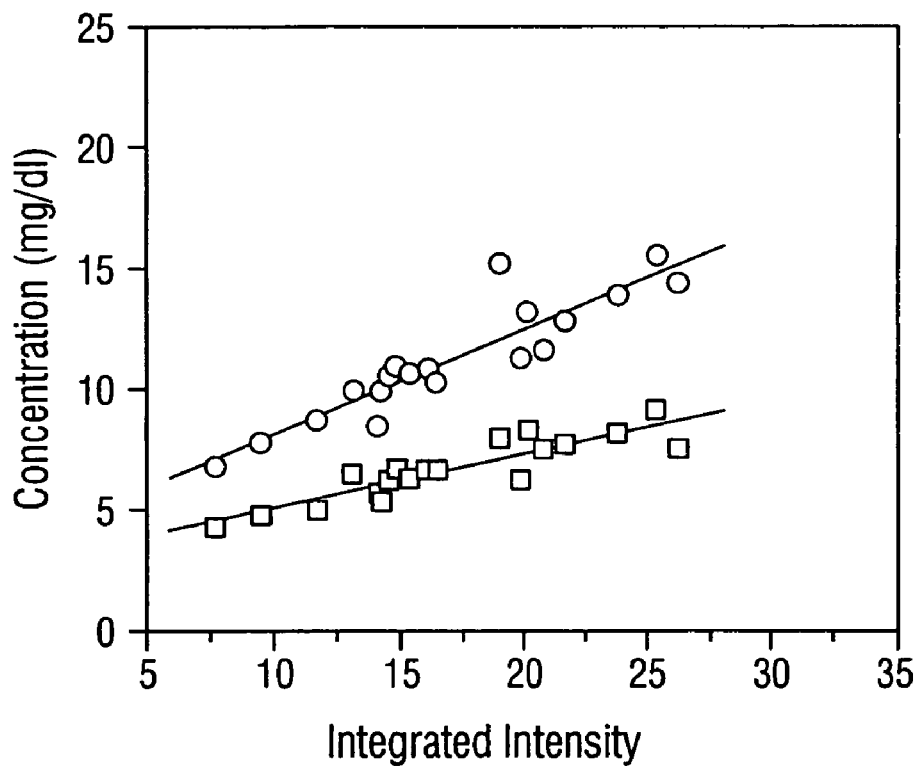
FIG. 3B is a plot of concentration against integrated intensity. The lines correspond to $LDL_{Chol} = 0.433x + 37.58$ $R^2 = 0.832$; $LDL_{B-100} = 0.222x + 28.90$ $R^2 = 0.789$. |
| 4 | Identification of LDL as a possible marker for cardiovascular health.

The VLDL, LDL and HDL fractions from each tube were assayed for cholesterol. The VLDL and LDL fractions from each tube were assayed for Apo B-100. Integrated areas of peaks in lipoprotein density profile correlated with cholesterol levels (FIG. 3).

Example 9

Capillary Electrophoresis Analysis

The fractions collected after ultracentrifugation can be further analyzed using capillary electrophoresis (CE). This can be used to identify sub-fractions of the lipoprotein fractions based on electrophoretic mobility. Phosphates or other buffers can be used to simulate physiological pH and salt conditions.

Example 10

Solid Phase Extraction

Solid phase extraction can be used to separate lipids and proteins, as it disrupts the lipoprotein particle structure. Elution is according to hydrophobicity of bound materials, and can be changed by increasing or decreasing the polarity of the eluent.

Apolipoprotein can be separated from lipids using a solid-phase extraction cartridge to effect a chromatographic separation of the components. Samples were delipidated by the following method.

The cartridge (tC18 Light, Sep-Pack, 36805, Waters, Milford, Mass.) was conditioned dropwise with 5 mL of 0.1% (v/v) TFA in acetonitrile allowing no air to enter the cartridge. The cartridge was then conditioned dropwise with 5 mL 0.1% (v/v) TFA in water allowing no air to enter the cartridge. A sample was prepared from the lipoprotein fractions and loaded slowly onto the cartridge. The fractions were as follows: VLDL: 325 µL fraction, 50 µL 0.1% TFA, 125 µL deionized water; LDL: 750 µL fraction, 50 µL 0.1% TFA, 150 µL deionized water; HDL: 100-200 µL fraction, 40-50 µL 0.1% TFA, 210-300 µL deionized water; Bottom: 30-50 µL fraction, 40-50 µL 0.1% TFA, 310-400 µL deionized water.

The cartridge was rinsed with 5 mL 0.1% (v/v) TFA in water to remove any salts and contaminants from the UC spin. Air was pushed through the cartridge to remove any remaining liquid. Proteins were then eluted in 50 µL aliquots of 0.1% TFA in acetonitrile. The second, third, and fourth aliquots contained the majority of apolipoproteins and were collected and combined. For examination of the elution curve, individual aliquots were collected and analyzed separately.

Example 11

Analysis of Lipids

Figure 10A:
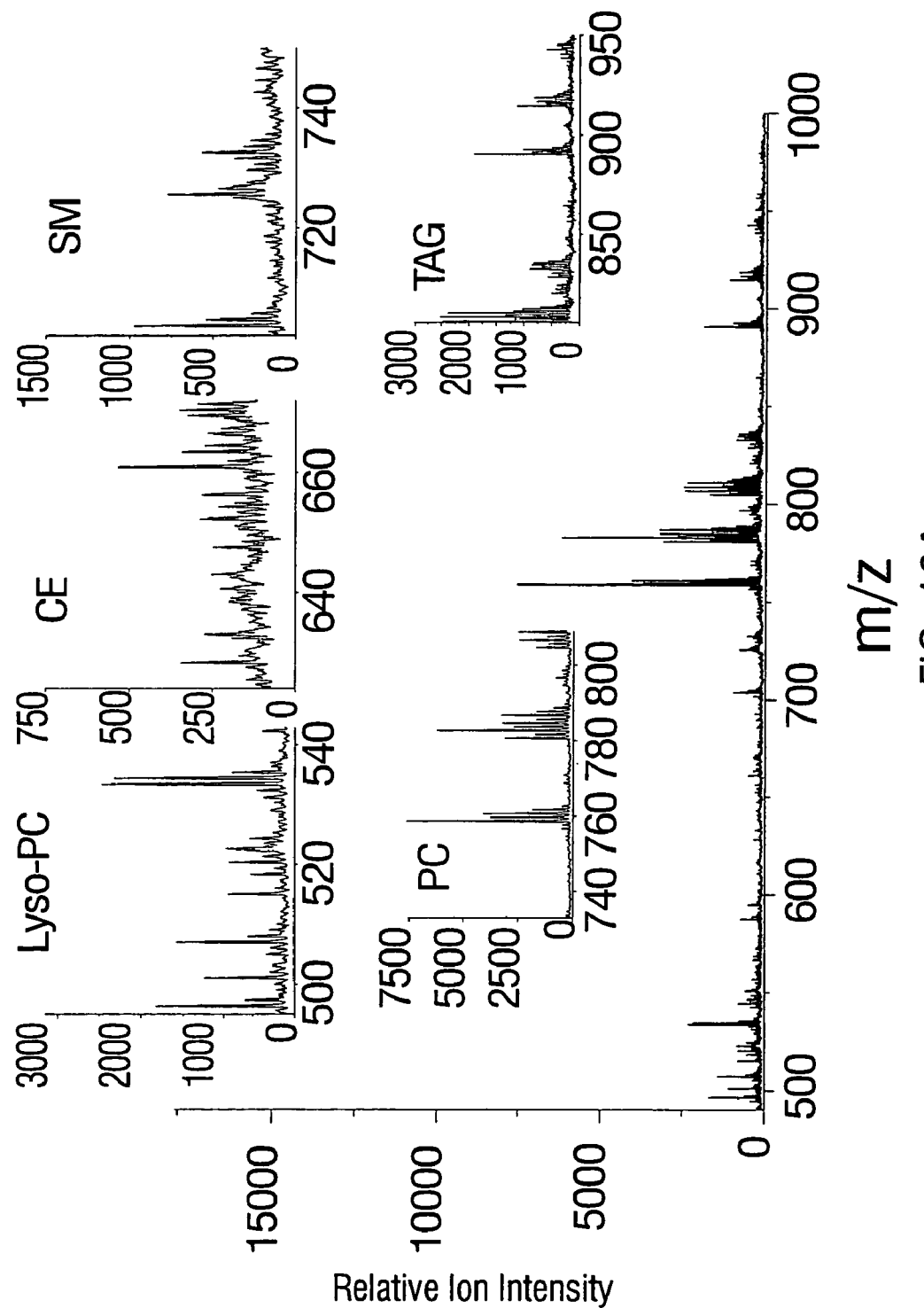
FIG. 10A is of HDL.
Figure 10B:
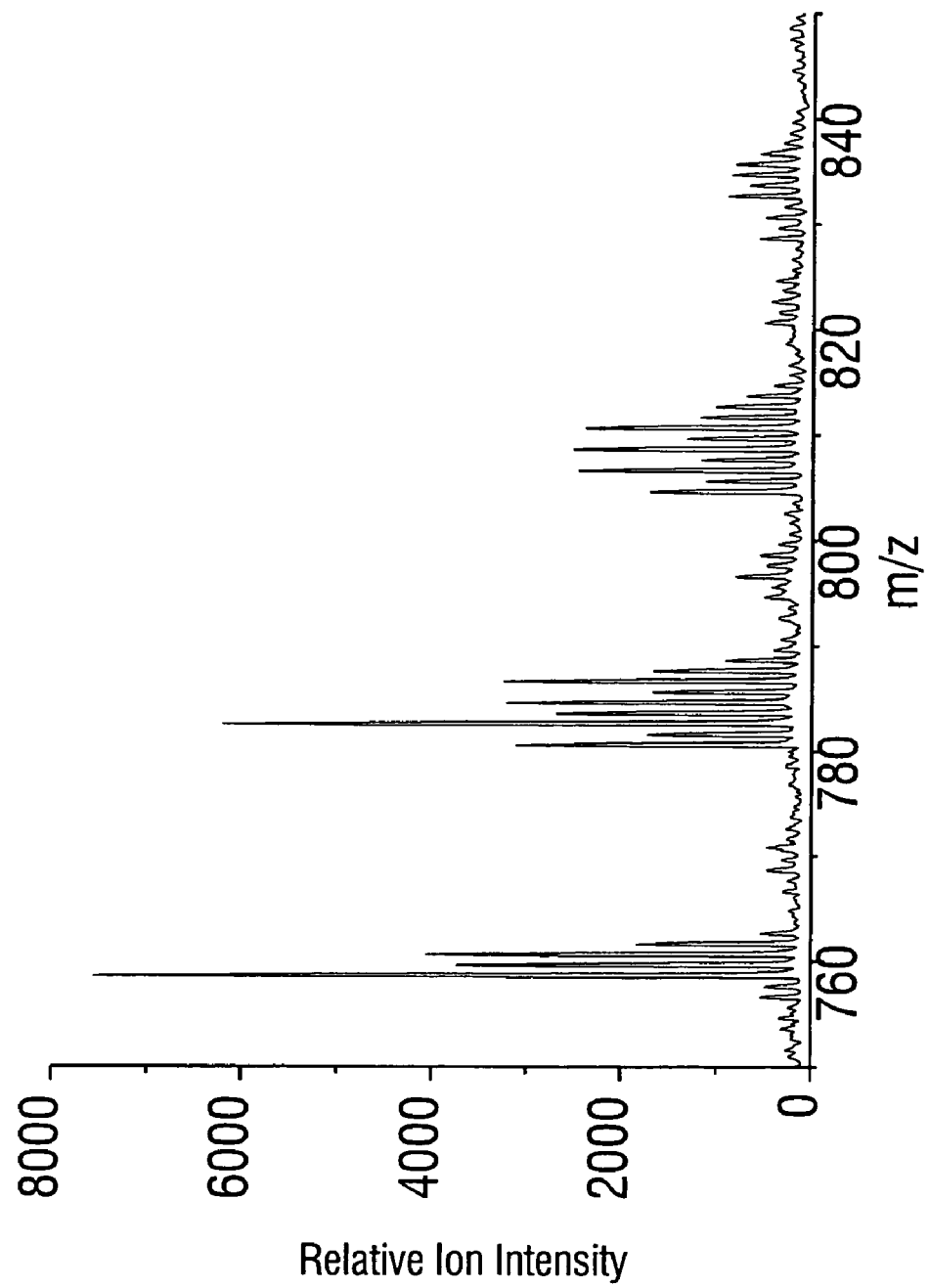
FIG. 10B is of phosphatidylcholine region. |
| 11 | Differential density gradient profile and immunoprecipitation of Lp(a).

Lipids left in the SPE cartridge can be recovered and analyzed using high performance thin layer chromatography, mass spectrometry (FIG. 10), and EPR. Recovery can be performed using elution with polar solvents such as chloroform, methanol, with hexane, isopropanol, ethyl ethers, or other solvents.

Example 12

IPG-IEF Assays

Lipoprotein fractions can be further separated by the pI value of the component proteins. Isoelectric focusing can be performed as follows.

Samples were evaporated to dryness and reconstituted in 255 µL of an 8 M urea (deionized with Amberlite), 2% (w/v) CHAPS solution. The samples were placed under sonication for 30 min at 20° C. The samples were incubated at room temperature for 30 minutes. The samples were spun for 5 min at 10,000 rpm. A 250 µL aliquot was applied to the sample holder, and a 13 cm, pH 4-7 Immobiline DryStrip was placed gel-down onto the sample. Mineral oil was used to cover the strip, and the sample holder cover was placed on top of the strip. IEF parameters for the separation were 50 µA per strip at 20° C. The protocol for the isoelectric focusing included a rehydration step for 12 hours followed by steps of 500 V·hr, 1000 V·hr, and 32000 V·hr.

Volumes of 355 µL and 350 µL were used for the reconstitution and loading steps for the IPG analysis using an 18 cm IPG strip. For pH 4-7, two IEF protocols were used including the one described above and a longer run including a rehydration step for 12 hours followed by steps of 500 V·hr, 1000 V·hr, 1000 V to 5000 V gradient for 30 minutes (1500 V·hr), 5000 V for 9 hours (45000 V·hr), and 6000 V for 1 hour (6000 V·hr). This longer protocol was also used for isoelectric focusing with an 18 cm pH 3-10 IPG strip.

Example 13

Acid Violet Staining of IPG Gels

Figure 7A:
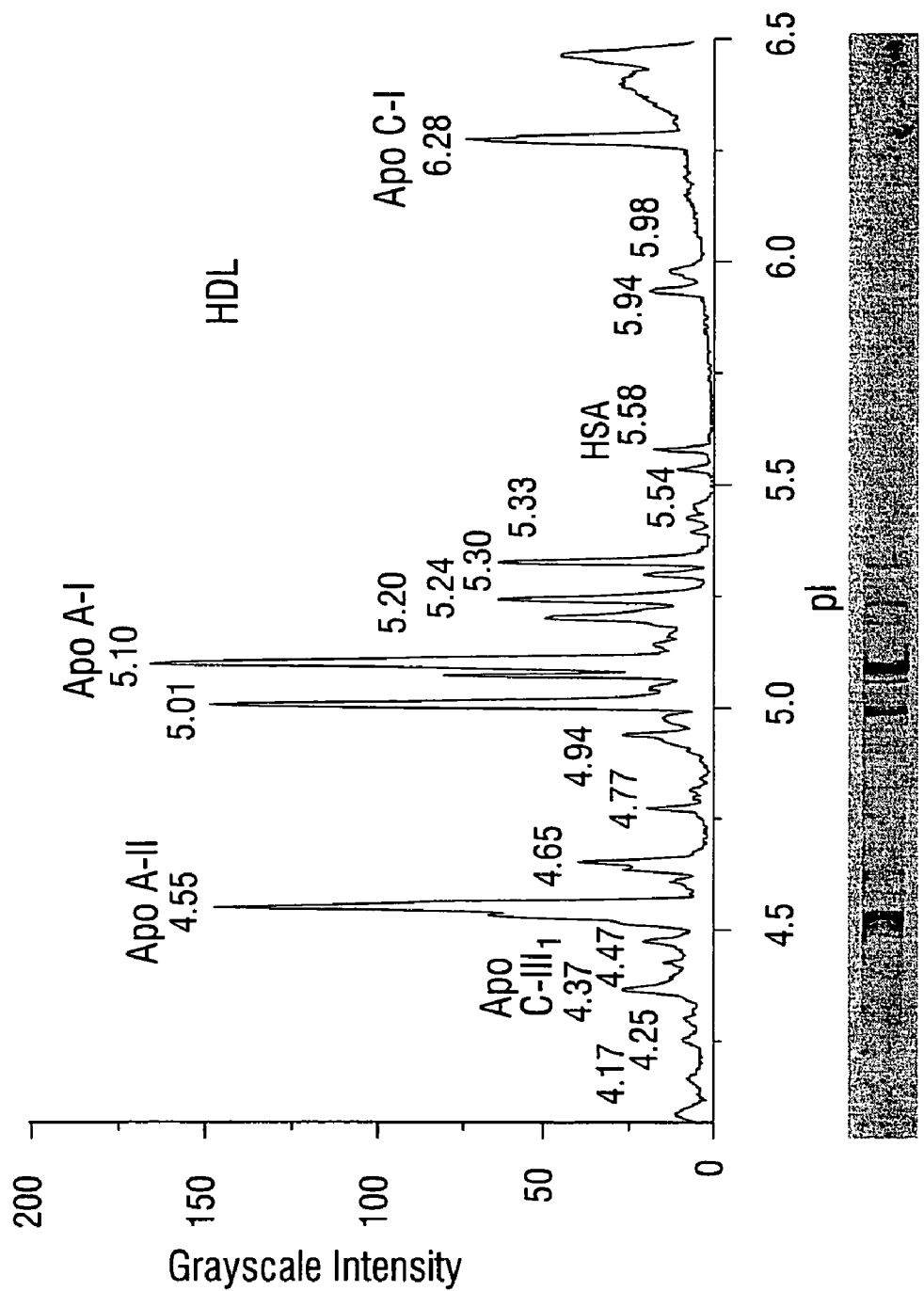
FIG. 7A is a plot of grayscale intensity against pI.
Figure 7B:
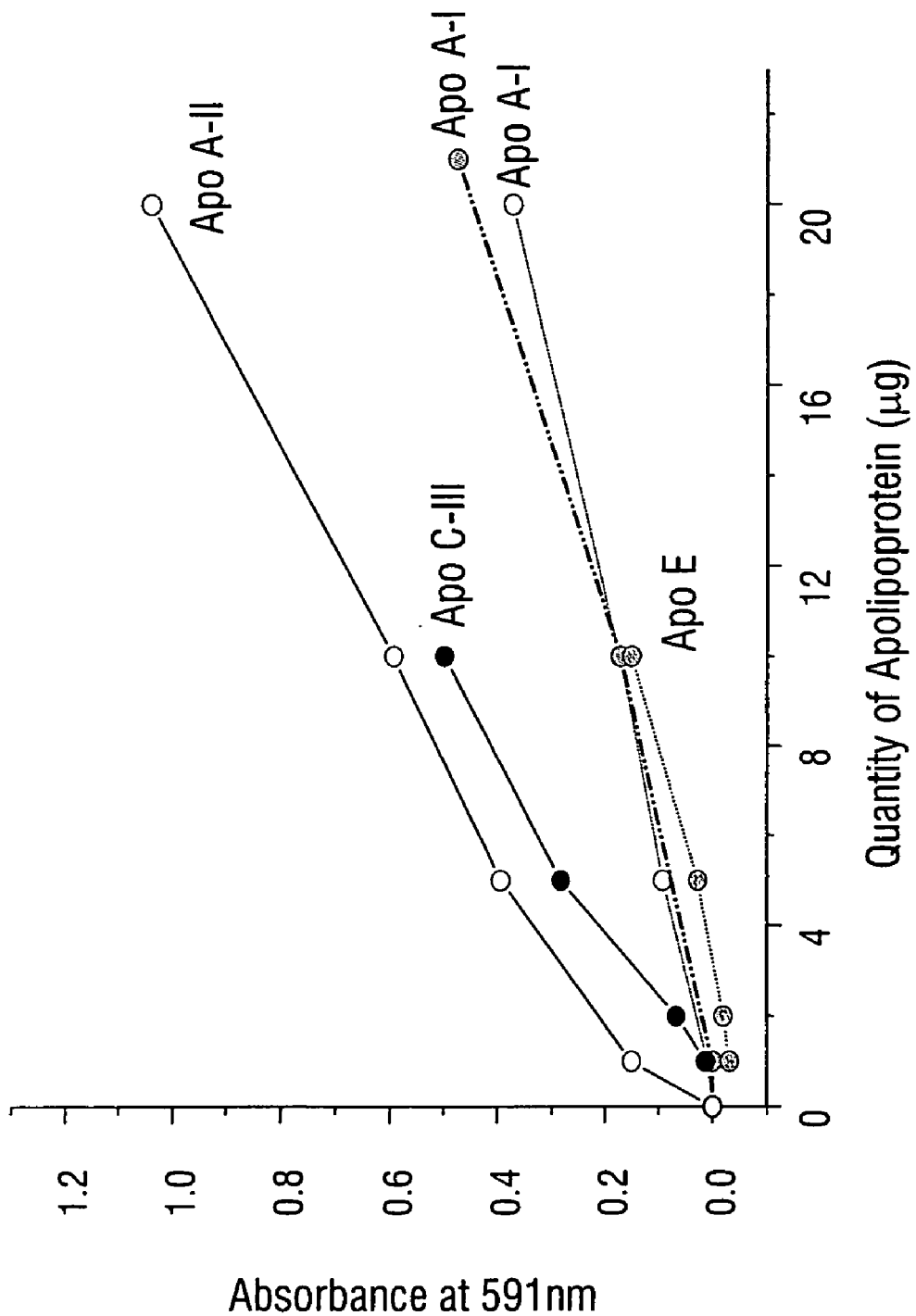
FIG. 7B is a plot of Absorbance at 591 nm against quantity of apolipoprotein (contains two plots for Apo A-I). |
| 8 | IPG gel scan and mass spectra of Apo A-II (FIG. 8A); Apo A-I (FIG. 8B); prealbumin and HSA (FIG. 8C); and Apo C-I and $SAA_4$ (FIG. 8D) recovered from the IPG gel |
| 9 | Imaging of 2-D SDS-PAGE gels |
| 10 | MALDI of lipids in HDL fraction.

A colloidal Acid Violet staining protocol was used for the visualization of the bands in the IPG gel. The gels were removed from the sample holders and fixed for 30 min in a 20% (w/v) trichloroacetic acid solution. The gels were then placed in a defixing solution, 3% (v/v) phosphoric acid, for one minute. The gels were stained using a colloidal Acid Violet solution comprised of approximately 100 mg Violet 17 dissolved in 50 mL deionized water mixed with 50 mL 20% (v/v) phosphoric acid for 10 minutes. The gels were de-stained for three 10 minute periods in 3% (v/v) phosphoric acid. The gels were rinsed for three 5 minute periods in deionized water. The gels were soaked in a 5% (v/v) glycerol solution for 20 min, then the excess glycerol was removed. Pictures of the gels on a light table were recorded with a digital camera. Imaging analysis was performed with software to produce a protein pH profile (FIG. 7). The pI values determined were based on the pH gradients provided by Amersham Biotech Pharmacia.

Example 14

Quantitation of Proteins by Dye Elution from IPG Gels

Protein-bound dye is extracted from section of the gel using mixtures of organic solvents. The extracted dye was quantified by absorbance measurements. Following imaging, gel fractions were cut out and separated from the plastic support using a scalpel. The gel fragments were placed in 1.5 mL tubes, and the dye was extracted into 500 µL volume of a formic acid, isopropanol, and water mixture. The extraction was carried out for 0.5 hour using occasional vortexing. A 300 µL volume of each extract was used to measure the absorbance at 591 nm. Calibration consisting of concentration vs. absorbance were plotted for each protein and their linearity was evaluated (FIG. 7).

Example 15

Passive Elution of Intact Proteins—Analysis Using Mass Spectrometry

Mass spectrometry is useful for identifying unusual bands appearing in pI profiles of lipoprotein fractions. Following the IPG separation, the unfixed and unstained gel was removed from the holder and placed on a flat surface for collecting the gel. The gel pieces were treated in the following manner. The gel pieces were washed with deionized water. The gel pieces were dehydrated with acetonitrile for 20 minutes with some vortexing. The gel pieces were washed with deionized water. The gel pieces were dehydrated with methanol for 20 minutes with some vortexing. The gel pieces were washed with deionized water. The proteins were extracted from the gel pieces with 100 µL FAPH for 15 min under sonication at 35° C. Following a 2 minute spin at 10,000 rpm, the supernatant was removed and evaporated to dryness. Samples were reconstituted in 6 µL FAPH. An aliquot was taken for MALDI analysis. For the analysis of the HDL fraction, segments of the gel were excised at the same position of corresponding bands in the fixed and stained gel.

Figure 8B:
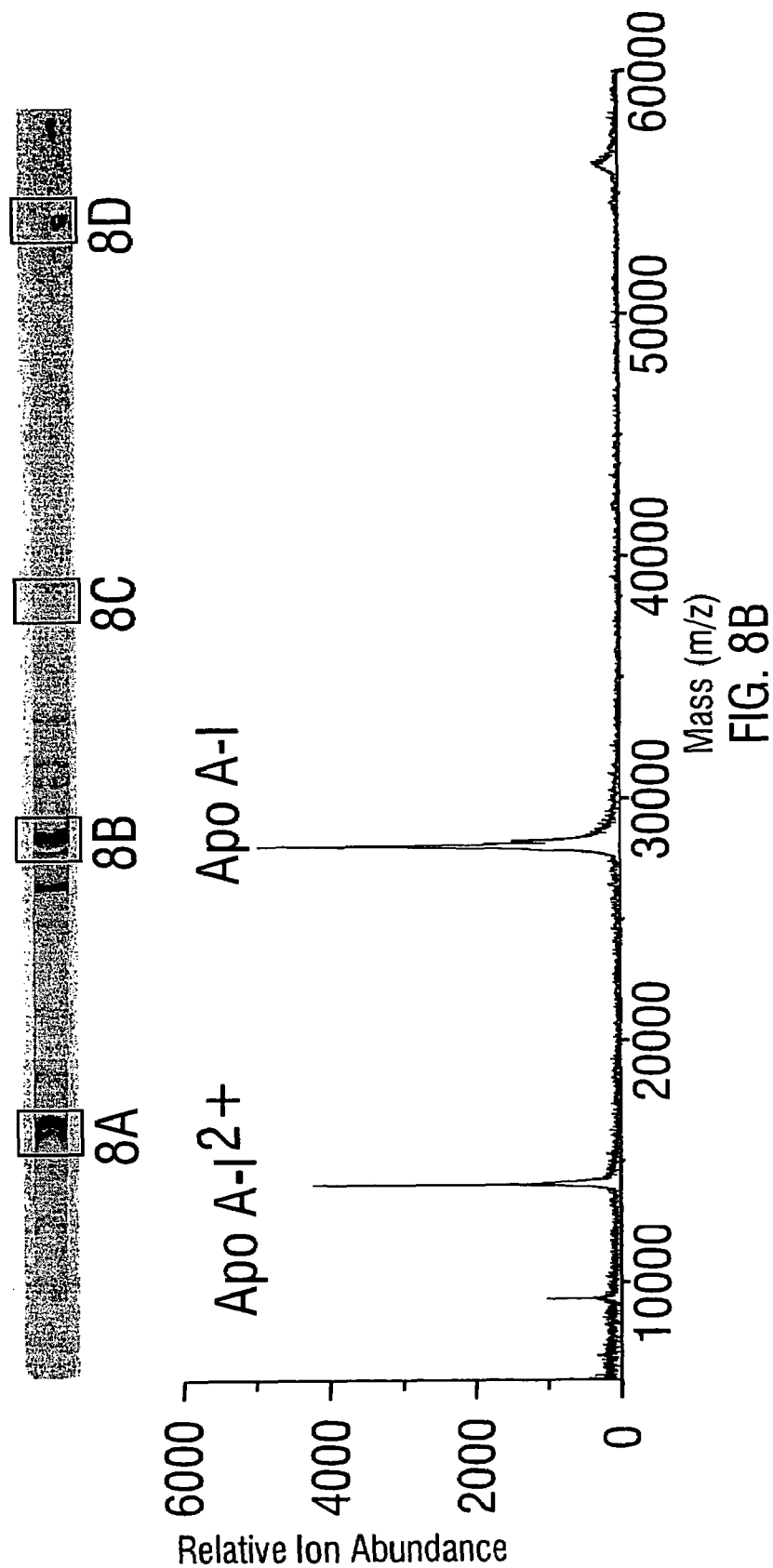
Figure 8C:
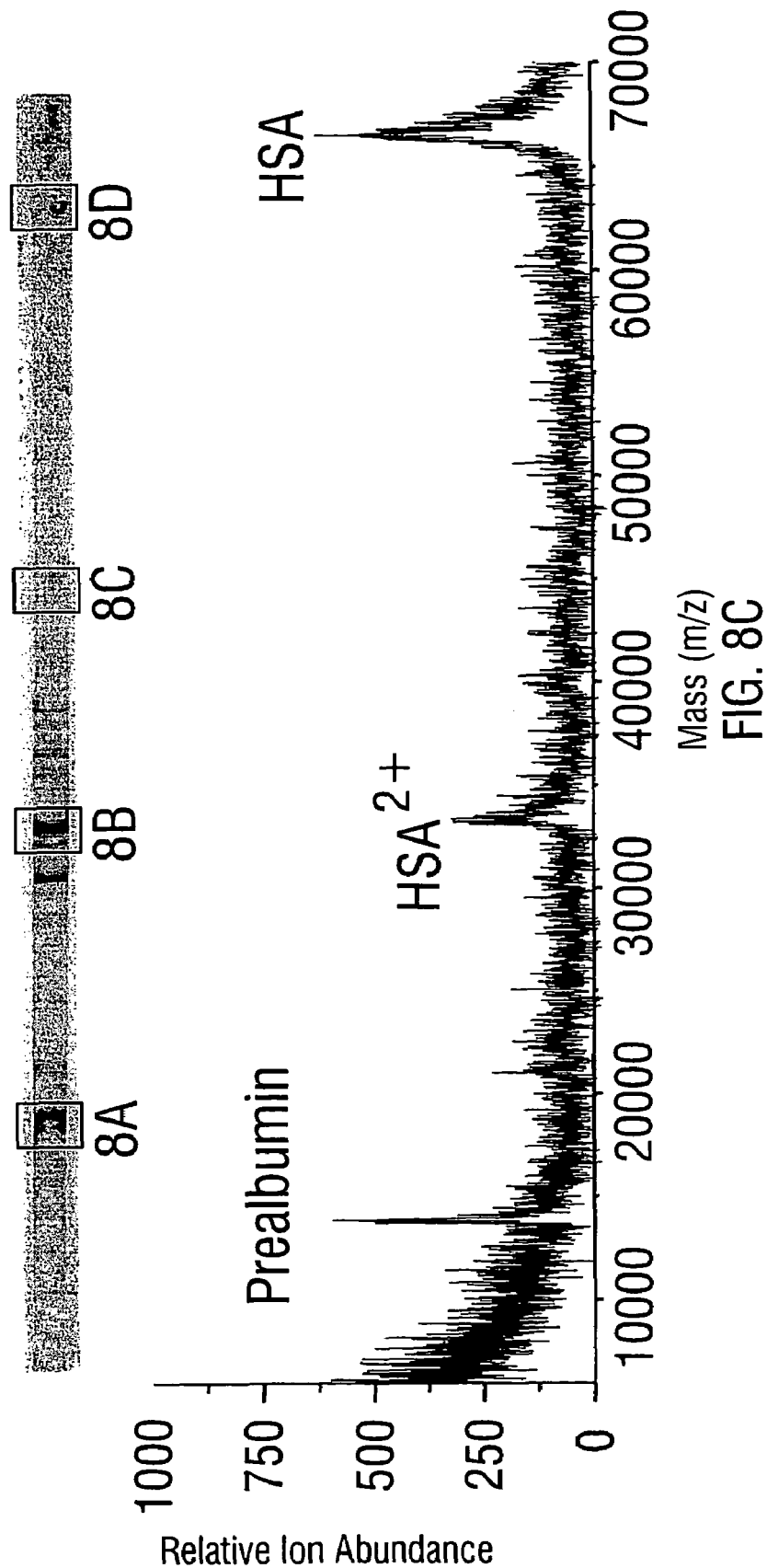
Figure 8D:

Bands which were excised from IPG gels which were previous fixed and stained were first treated with the following steps prior to protein extraction. The dye was removed by incubating the band in a 1:1 (v/v) dioxane/water mixture with some vortexing for 3 hours. The band was then treated with FWI (mixture of 1:3:2 (v/v) formic acid/water/2-propanol) for 30 minutes. The protein was then extracted from the band with FAPH for 20 minutes under sonication at 35° C. An aliquot from the supernatant was used for MALDI analysis (FIG. 8). Proteins from individual bands were recovered intact with little or no modifications to the molecular weight as detected using MALDI-TOF MS (FIG. 8). This method could be used to identify novel bands detected in the pI profile.

Example 16

Two Dimensional Gel Electrophoresis

In order to combine the first and second dimension, an equilibration step is utilized. The proteins are focused at their pI values and are therefore neutral; the SDS coats the protein in order to provide the negative charge necessary for migration in the second dimension. A reduction of any disulfide bonds is also performed during these steps followed by removal of any excess reducing agent. The equilibration was performed using the following method. The unfixed and unstained IPG gel was removed from the holder and the excess cover fluid was removed. The gel was then placed in a test tube, film side down. A 10 mL aliquot of equilibration buffer (6 M urea, 30% (w/v) glycerol, 2% SDS, 50 mM Tris-HCl, pH 8.0 and a trace of bromphenol blue) was added to the tube containing 100 mg DTT (1% w/v). The tube was incubated horizontally to cover the gel with solution for 15 min with gentle shaking. The solution was decanted from the tube following the incubation. A 10 mL aliquot of equilibration buffer was added to the tube containing 400 mg iodoacetamide (4% w/v). The tube was incubated for 15 min with gentle shaking. The solution was decanted from the tube following the incubation. Excess liquid was removed from the gel prior to loading onto the second dimension.

Two-dimensional SDS-polyacrylamide gel electrophoresis was performed using standard methods on the Bio-Rad Protean II XL system (18.3 cm×19.3 cm gels). A 25 mM Tris-HCl, 192 mM glycine, 0.1% (w/v) SDS electrode buffer was prepared by diluting the 10× stock with deionized water. The coolant core of the cell was filled with common antifreeze. A pre-cast gel was prepared for electrophoresis by inserting the glass sandwich into the holders. The comb was removed and the well was rinsed repeatedly with deionized water to remove any unpolymerized polyacrylamide. The gel was then put into the cell apparatus. Molecular weight markers (3-5 µL) were loaded onto a small square of blotting paper and were allowed to dry. The paper was then loaded onto the top left side of the gel. The equilibrated IPG strip was loaded onto the gel using forceps with the gel side toward the glass plate (outward) and was sealed with a small amount of melted 0.5% (w/v) agarose in electrode buffer. Once the gel was cooled, the upper buffer chamber was filled with approximately 350 mL electrode buffer. The lower buffer chamber was filled to approximately 2 cm above the bottom of the gel with electrode buffer. The power source was programmed to run at a constant current by setting limits of 1000 V, 20 mA (per gel), and 80 W for 30 minutes followed by 1000 V, 30 mA (per gel), and 80 W for 4 hours. The gel was run until the dye front reached approximately 1 cm from the bottom of the gel. The gel was removed from the apparatus and the glass sandwich was opened with a gel knife to release the gel for visualization.

For the 18 cm strips, no molecular weight markers were used in the gel run, and 3 mm were cut from both ends of the IPG gel to match the dimensions of the SDS-PAGE gel. The clinical samples were analyzed using this 18 cm strip protocol.

Silver staining was performed with all steps taking place in a covered plastic container with gentle shaking. The gel was removed from the glass sandwich and fixed for 1 h in 10% (v/v) acetic acid, 40% (v/v) ethanol. The gel was rinsed in 30% (v/v) ethanol for 20 min twice. The gel was rinsed in deionized water for 20 minutes. The gel was sensitized by incubation in 0.02% (w/v) sodium thiosulfate for 1 minute. The gel was rinsed three times with deionized water for 20 seconds. The gel was incubated for 20 min in cold 0.1% (w/v) silver nitrate at 4° C. The gel was rinsed three times with deionized water for 20 sec, then for 1 minute. The gel was developed in 3% (w/v) sodium carbonate, 0.1% (v/v) formaldehyde for 3-6 minutes. The gel was rinsed with deionized water for 20 seconds. The development was stopped with 5% (v/v) acetic acid for five minutes. The gel was rinsed three times with deionized water for 10 minutes. The gel was stored at 4° C. in 1% (v/v) acetic acid until further analysis.

The stained gels were either scanned into the computer or recorded with a digital camera using a light table (FIG. 9). An HDL fraction from an apparently healthy individual was analyzed using these methods and was scanned into the computer (FIG. 9). The pattern of spots is similar to that expected for a lipoprotein fraction with the possible detection of some novel protein populations.

Example 17

Measurement of Lipid Peroxidation

Mass spectrometry, including MALDI or LC-MS, thin layer chromatography and EPR with spin trapping can be used to monitor lipid peroxidation. LDL peroxidation is a known risk factor for cardiac disease. Analysis may aid in the identification of the source and location of oxidation in the lipoprotein particle (i.e. lipid class, fatty acid content).

Example 18

Mass Spectrometry of Proteins

Figure 5A:
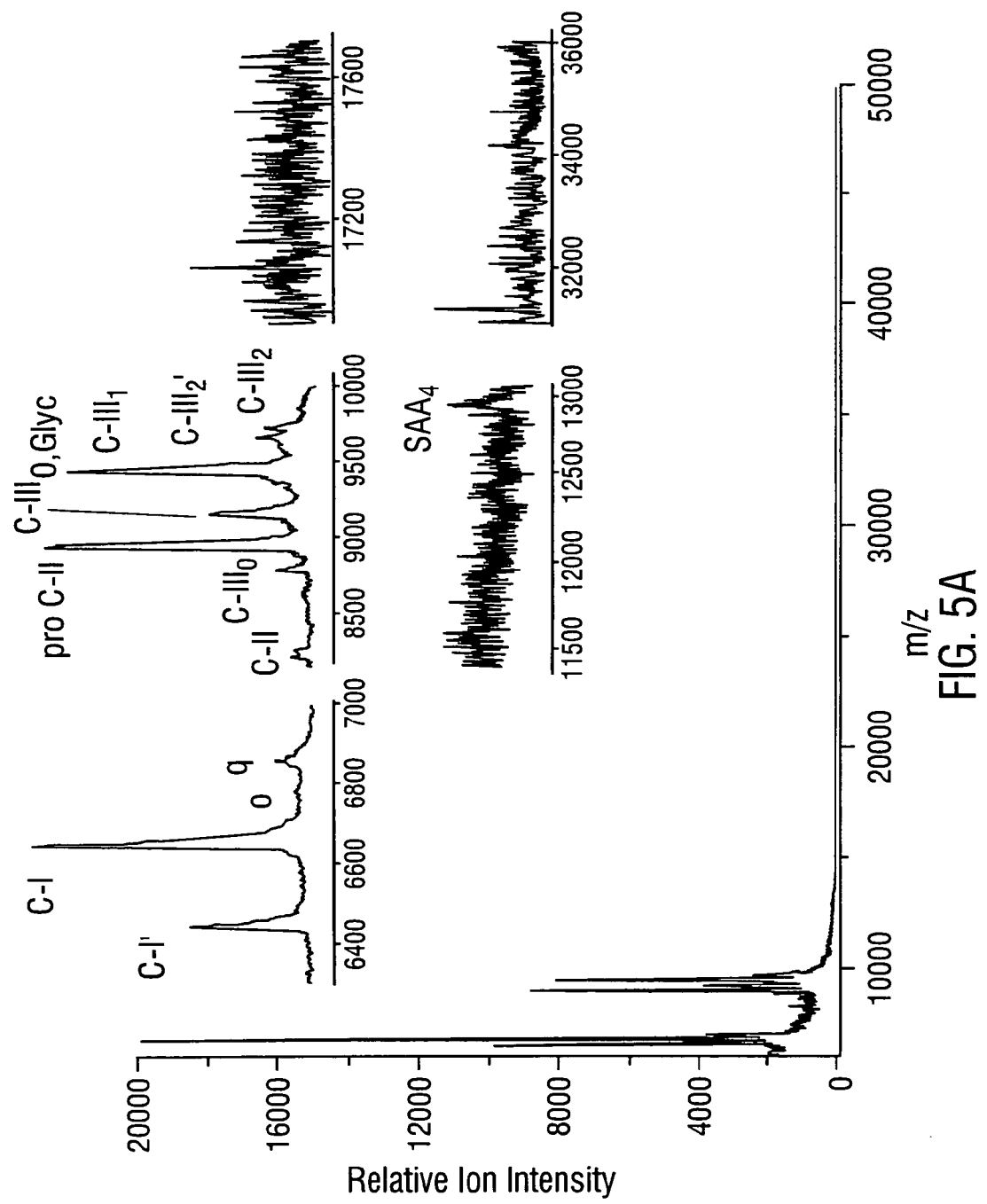
Figure 5B:
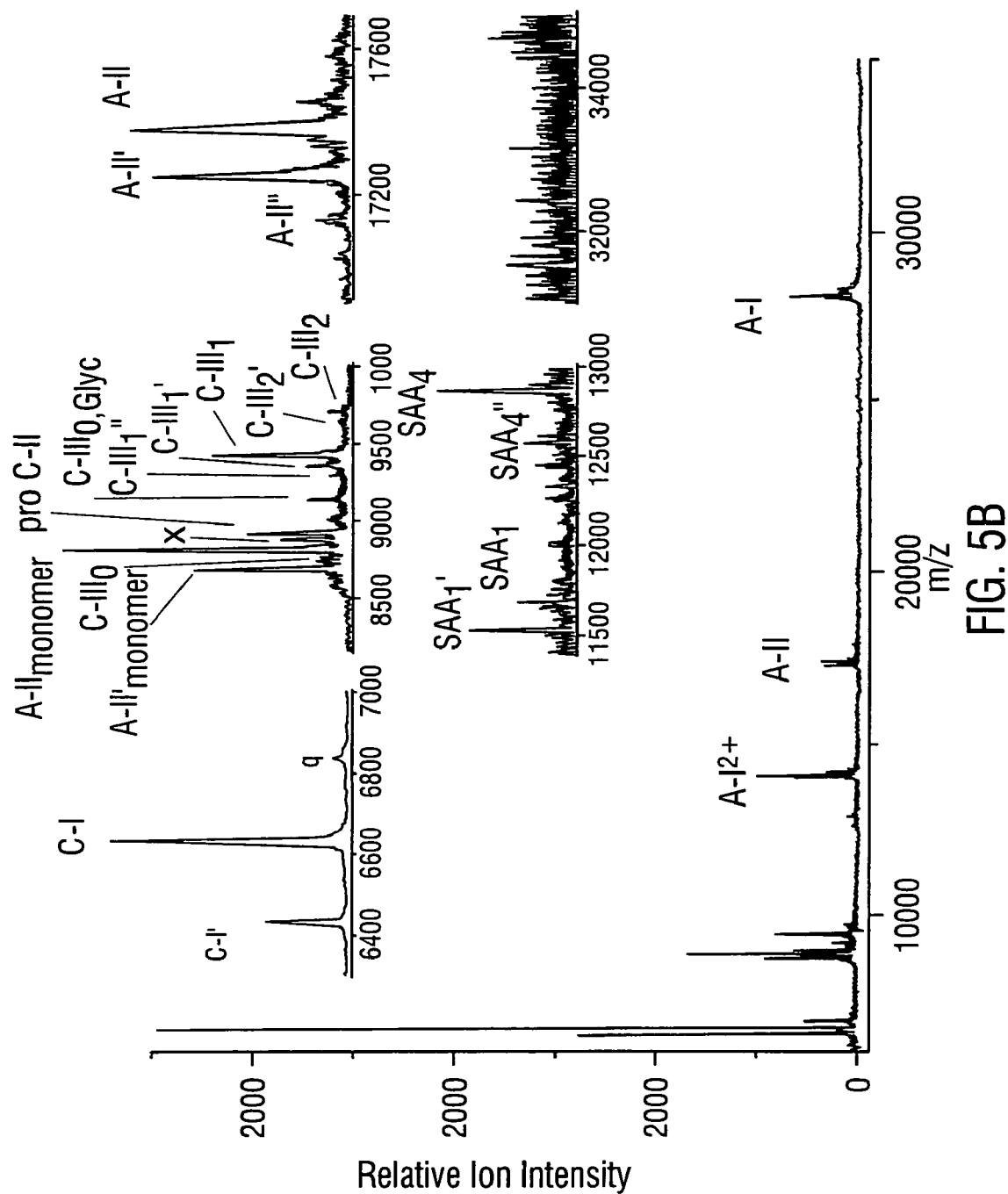

The protein samples were analyzed with a commercial MALDI-TOF mass spectrometer in the linear mode. A thin-layer sample preparation method was used for the MALDI analysis. A 0.5 µL aliquot of 35 mg/mL sinapinic acid was deposited on the target and allowed to dry. The samples were prepared by mixing 2 µL of the eluted fraction with 3 µL of a 25-mg/mL sinapinic acid matrix solution and 6 µL deionized water. A 0.5 µL aliquot of the same sample mixture was applied to the plate and allowed to dry followed by a 2 µL deionized water rinse. Myoglobin was used as an external mass calibration standard. The relative ion intensities of VLDL and HDL are shown in FIG. 5. The mass spectra of the two lipoprotein fractions show highly resolved isoforms of the apolipoproteins. Novel isoforms of some of the apolipoproteins were discovered using this method.

Example 19

Quantitation Using Enzymatic or Chemical Digestion

Figure 6:
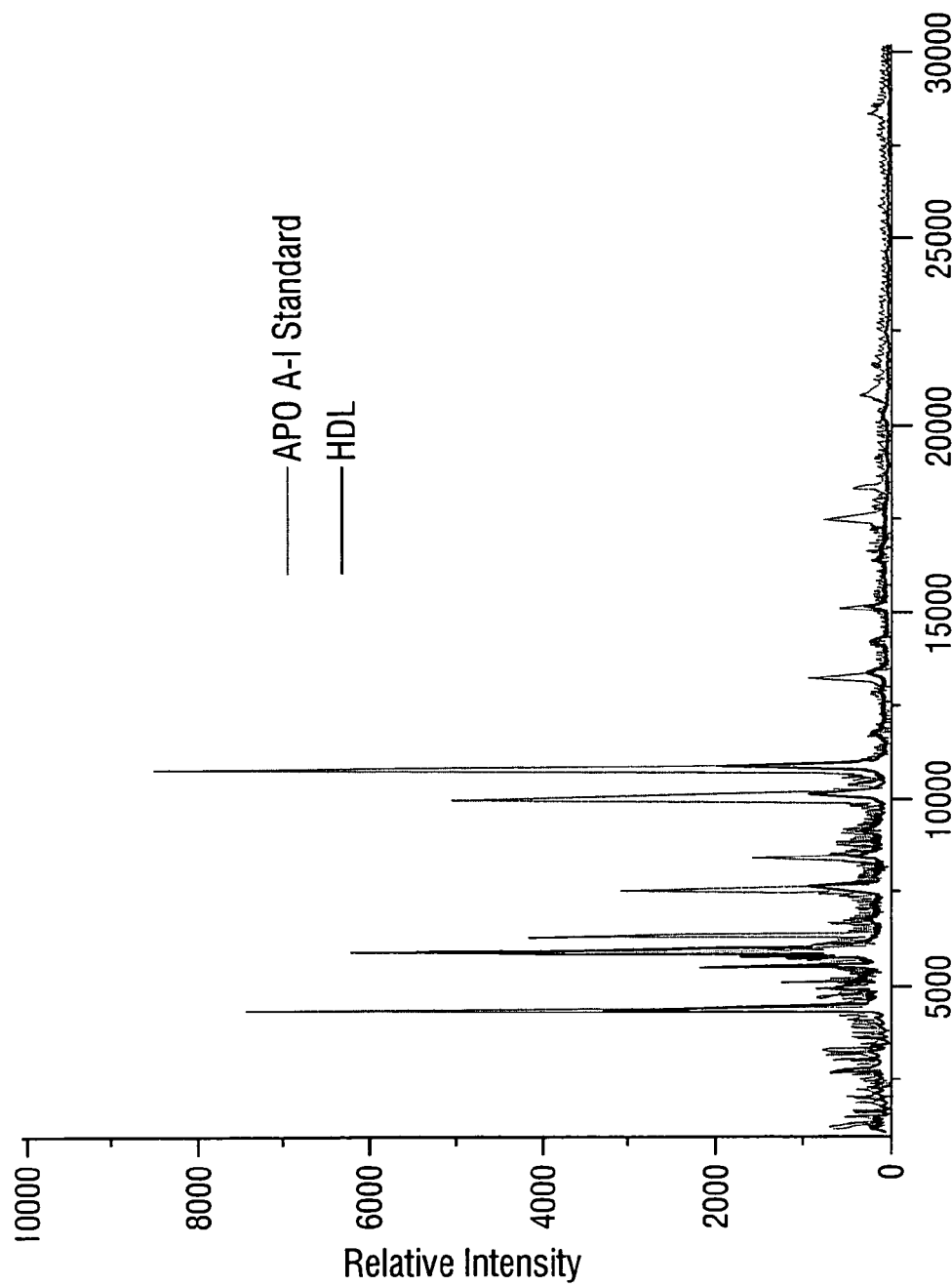

Proteins can be cleaved using enzymatic or chemical methods. Labeled or unlabeled peptide standards can be added to act as internal standards for use in mass spectral analysis. FIG. 6 shows the comparison of a chemically digested Apo A-I commercial standard and an HDL sample demonstrating the feasibility of digesting the apolipoproteins for this analysis. Internal standard peptides have not yet been introduced but have been used by others for quantitation in this fashion.

Example 20

Differential Density Profiling

22 µl serum are diluted with 185 µl 5 mM phosphate buffer (PB). 150 µl (diluted 2:3 with 5 mM PB) of a monoclonal anti-Lp(a) antibody are added to the sample. For the control sample add 150 µl of 5 mM PB (instead of antibody). The samples are incubated for 10 minutes at 32° C. After the incubation period, the Lp(a)-antibody complex is pelleted down by centrifuging the samples for 3 minutes at 14,000 rpm. The supernatant is transferred to a new eppendorf tube where 5 µl NBD are added. The samples are incubated at room temperature for 30 minutes, and then 400 µl of 5 mM PB are added. 550 µl of the stained solution are homogeneously mixed with 550 µl 20% CsBiY and ultracentrifuged for 4 hours and 40 minutes at 120,000 rpm and 20° C.

Figure 11A:
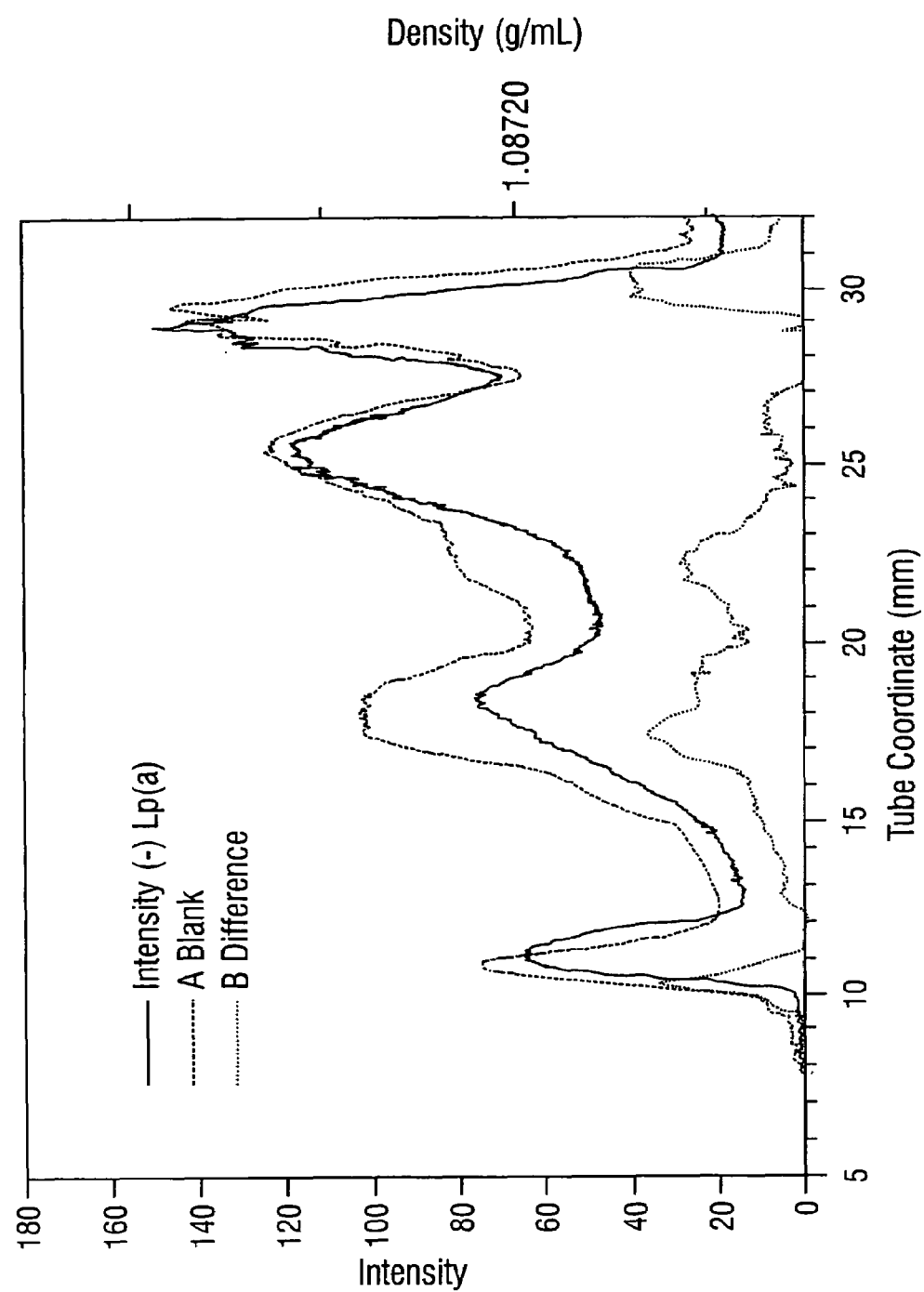
FIG. 11A is a Lp(a) immunoprecipitation with Lp(a) - 294 mg/dL.
Figure 11B:
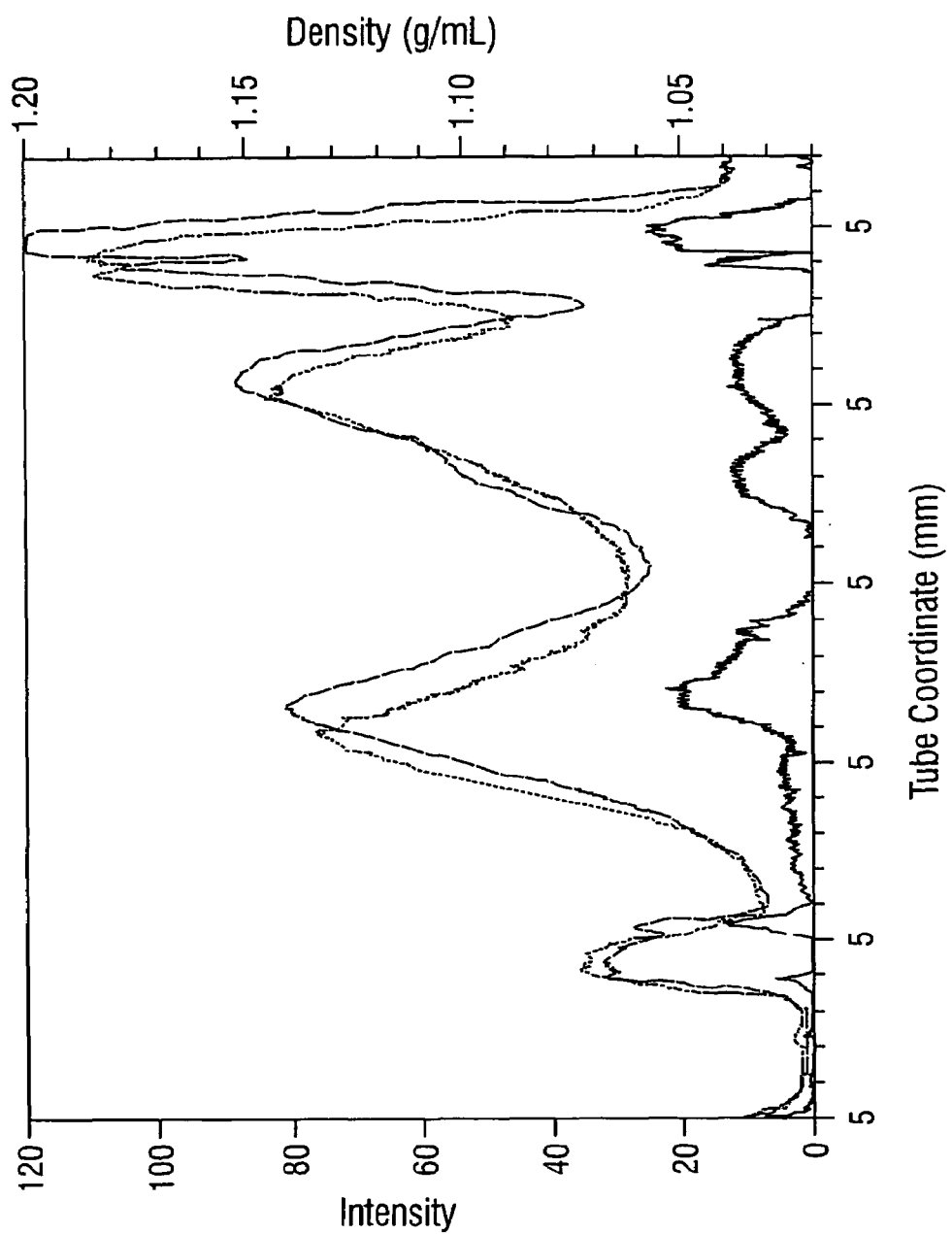
FIG. 11B is a reproducibility study of four samples immunoprecipitated with DiaSorin monoclonal antivirus.
Figure 11C:
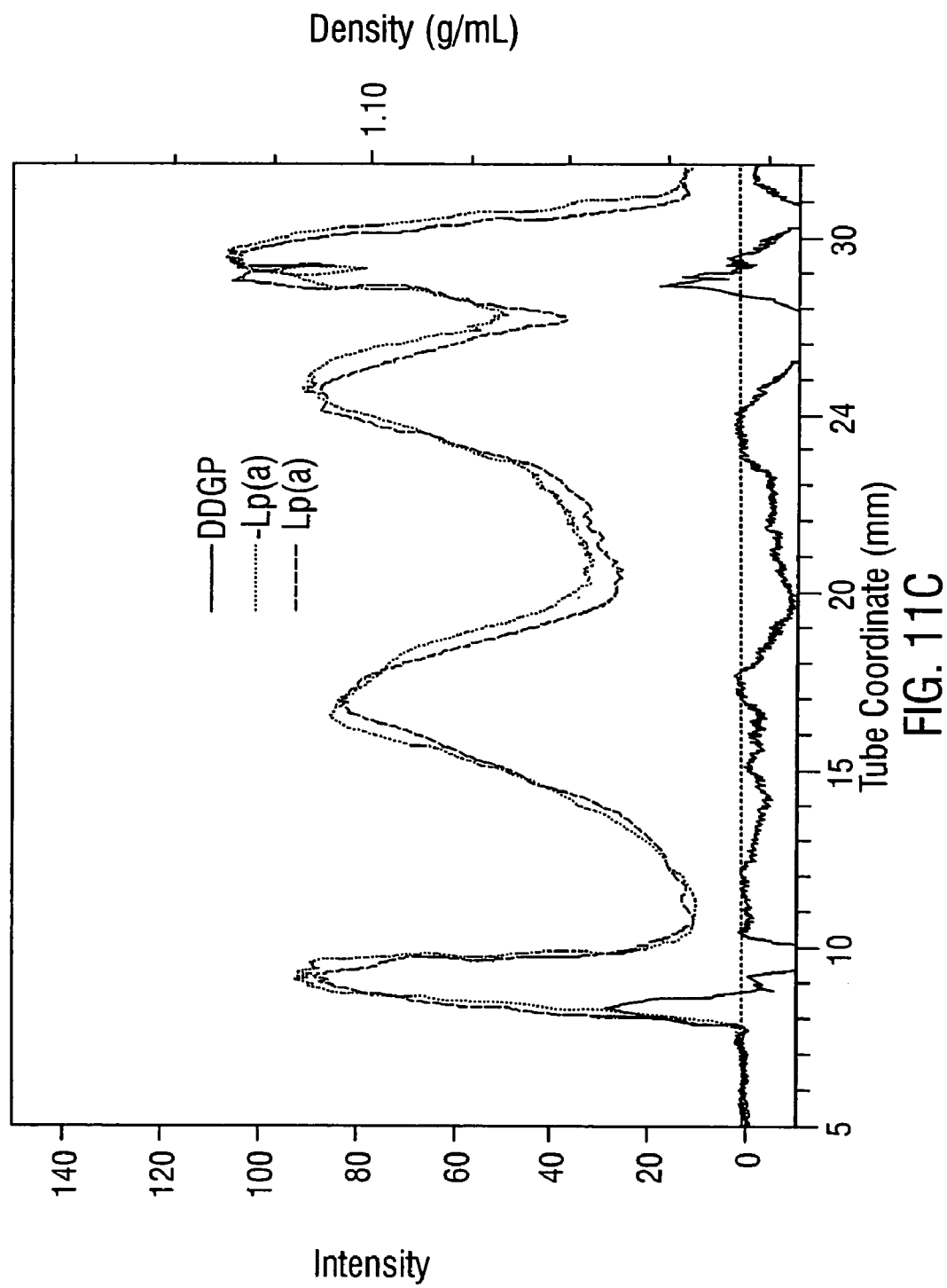
FIG. 11C is a differential density gradient profile of monoclonal antibody immunoprecipitation. |
| 12 | Diagram of lipoprotein analyses. The numbers on the diagram do not imply a specific required order of steps. The numbers on the diagram correspond to the following analyses: 1—ultracentrifuge separation; 2—digital imaging and analysis to generate lipoprotein density profile; 3—fraction collection; 4—quantitation; 5—density determination; 6—VLDL fraction; 7—LDL fraction; 8—HDL fraction; 9—protein fraction; 10—capillary electrophoresis (CE); 11—solid phase extraction; 12—lipids fraction; 13—mass spectrometry; 14—thin layer chromatography; 15—electron paramagnetic resonance (EPR); 16—mass spectrometry; 17—immobilized pH gradient isoelectric focusing; 18—passive elution/MALDI; 19—protein quantitation by dye elution; 20—two dimensional gel electrophoresis. |

A differential density gradient profile (DDGP) is obtained by subtracting the Lipoprotein Density Gradient Profiles (Control sample—immunoprecipitated Lp(a) sample). The sample density distribution of apo(a) isoforms is resolved in the DDGP (FIG. 11).

Example 21

Analysis of Cord Plasma Samples

Cord plasma can be used to analyze lipoprotein heterogeneity at birth. Assays performed on 163 infants revealed a subgroup of infants having a prominent peak of large HDL that is enriched in apoC-I. Tracking of the health of these infants may reveal a correlation of the presence or absence of the apoC-I enriched HDL particle with various disease states.

Example 22

Monitoring of Diet and Lifestyle Effects

The above described methods for determining the lipid profile of an individual can be used to monitor the effects of changes in diet and/or lifestyle in an individual. Periodic sampling of plasma can show alterations in the lipid distribution resulting from the change in diet and/or lifestyle.

Figure 4A:
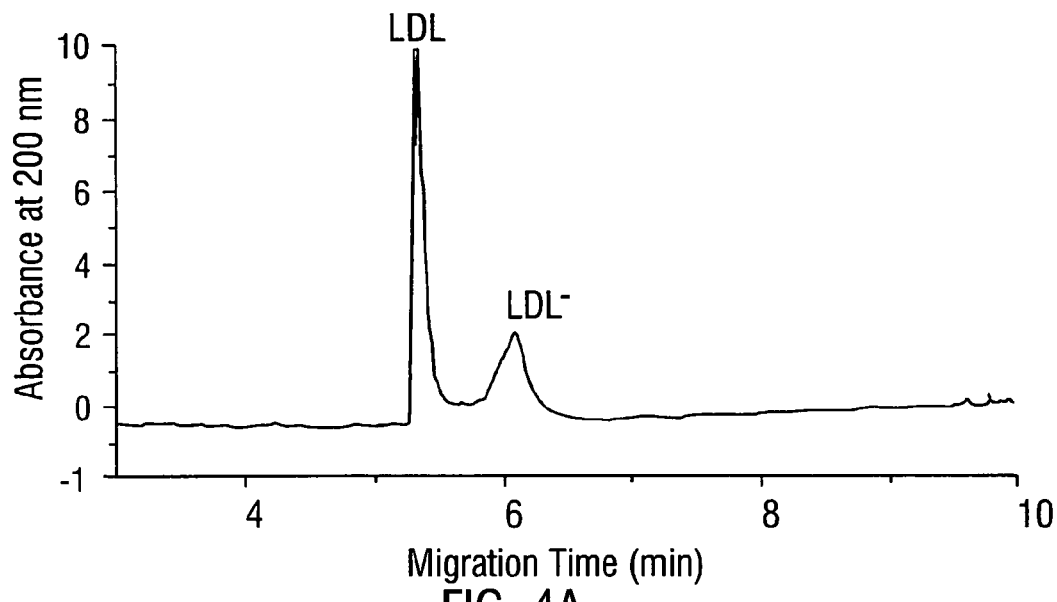
FIG. 4A is of a healthy individual.
Figure 4B:
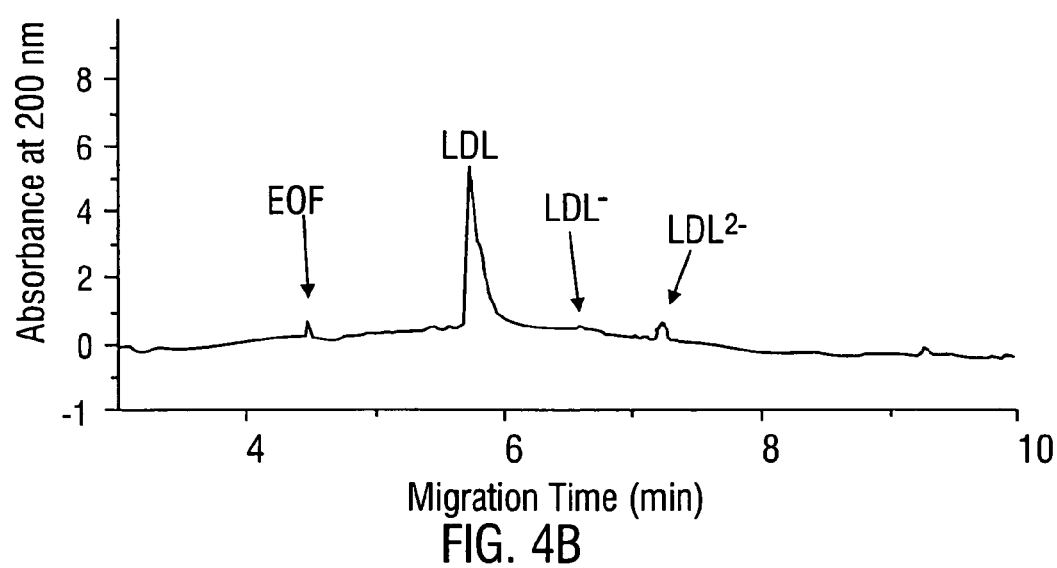
FIG. 4B is of an unhealthy individual. |
| 5 | Mass spectrometry of VLDL (FIG. 5A) and HDL (FIG. 5B) samples |
| 6 | Mass spectrometry of chemically digested Apo A-I standard and HDL samples |
| 7 | IPG gel scan and quantitation of apolipoprotein.

Comparison of the LDL levels in apparently healthy and unhealthy individuals with documented cardiovascular disease showed significant differences by CE analysis (FIG. 4).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. A method of obtaining the lipoprotein profile of a sample, the method comprising:
    contacting the sample, a metal ion chelate complex density gradient forming agent, and a dye to produce an unseparated mixture, wherein the sample contains lipoproteins;
    subjecting the unseparated mixture to a centrifuge force field under conditions suitable to produce a separated mixture, wherein the separated mixture comprises multiple lipoprotein fractions; and
    visualizing by photographing or digital imaging the multiple lipoprotein fractions to obtain a lipoprotein profile.

2. The method of claim 1, wherein the density gradient forming agent is a metal EDTA salt.

3. The method of claim 2, wherein the density gradient forming agent is an alkali metal EDTA salt.

4. The method of claim 3, wherein the density gradient forming agent is a sodium metal EDTA salt.

5. The method of claim 4, wherein the density gradient forming agent is NaCuBDTA, NaFeEDTA, or NaBiEDTA.

6. The method of claim 1, wherein the sample is a plasma sample or serum sample.

7. The method of claim 1, wherein the dye is a visible dye.

8. The method of claim 1, wherein the dye is a fluorescent dye.

9. The method of claim 7, wherein the dye is NBD $C_6$-ceramide or Sudan Black B.

10. The method of claim 1, wherein the unseparated mixture further comprises a buffer.

11. The method of claim 1, wherein the centrifuge force field is at least about 400,000×g.

12. The method of claim 11, wherein the centrifuge force field is about 400,000×g to about 600,000×g.

13. The method of claim 1, wherein the multiple lipoprotein fractions comprise one or more of the group consisting of a VLDL fraction, a IDL fraction, a LDL fraction, a Lp(a) fraction, and a HDL fraction.

14. The method of claim 1, wherein the visualizing step comprises digital imaging and analysis of the separated mixture.

15. The method of claim 1, wherein the visualizing step comprises digital imaging by scanning the separated mixture.

16. The method of claim 1, further comprising freezing the separated mixture and slicing the separated mixture, wherein the freezing and slicing steps are performed after the visualization step.

17. The method of claim 1, further comprising analyzing one or more of the multiple lipoprotein fractions.

18. The method of claim 17, wherein the analyzing step comprises capillary electrophoresis, mass spectrometry, thin layer chromatography, electron paramagnetic resonance (EPR), immobilized pH gradient isoelectric focusing, matrix assisted laser desorption/ionization (MALDI) mass speotrometry, electrospray ionization mass spectrometry (ESI-MS), or two dimensional gel electrophoresis.

19. A method of separating total lipoprotein in a serum sample from non-lipoprotein serum proteins, the method comprising:
    contacting a serum sample, a metal ion chelate complex density gradient forming agent, and a dye to produce an unseparated mixture, wherein the serum sample contains lipoproteins; and
    subjecting the unseparated mixture to a centrifuge force field under conditions suitable to produce a separated mixture, wherein the separated mixture comprises sedimented non-lipoprotein serum proteins and non-sedimental lipoproteins;
    wherein the dye aids in visualizing the lipoproteins in the separated mixture.

20. The method of claim 19, wherein the density gradient forming agent is a metal EDTA salt.

21. The method of claim 20, wherein the density gradient forming agent is an alkali metal EDTA salt.

22. The method of claim 21, wherein the density gradient forming agent is a sodium metal EDTA salt.

23. The method of claim 22, wherein the density gradient forming agent is NaCuEDTA, NaFeEDTA, or NaBiEDTA.

24. The method of claim 19, wherein the unseparated mixture has a density of at least about 1.3 kg/m$^3$.

25. A method of obtaining a differential density lipoprotein profile of a sample, the method comprising:

contacting the sample, a metal ion chelate complex density gradient forming agent, and a dye to produce a first unseparated mixture, wherein the sample contains lipoproteins;

subjecting the first unseparated mixture to a centrifuge force field under conditions suitable to produce a first separated mixture, wherein the first separated mixture comprises a first set of multiple lipoprotein fractions;

visualizing by digital imaging the first set of multiple lipoprotein fractions to obtain a first lipoprotein profile;

contacting the sample and an antibody that binds to a lipoprotein fraction to form an antibody-lipoprotein complex;

separating the antibody-lipoprotein complex from the sample to produce a reduced sample;

contacting the reduced sample, a metal ion chelate complex density gradient forming agent, and a dye to produce a second unseparated mixture;

subjecting the second unseparated mixture to a centrifuge force field under conditions suitable to produce a second separated mixture, wherein the second separated mixture comprises a second set of multiple lipoprotein fractions;

visualizing by digital imaging the second set of multiple lipoprotein fractions to obtain a second lipoprotein profile; and subtracting the second lipoprotein profile from the first lipoprotein profile to obtain a differential density lipoprotein profile.

26. The method of claim 25, wherein the sample is a plasma sample or serum sample.

27. The method of claim 25, wherein the antibody is a monoclonal antibody or a polyclonal antibody.

28. The method of claim 25, wherein the antibody-lipoprotein complex is separated by immunoprecipitation, paramagnetic beads, gel filtration chromatography, or antibody capture chromatography.

29. The method of claim 25, wherein the antibody-lipoprotein complex is separated by immunoprecipitation.

30. The method of claim 25, wherein the density gradient forming agent is a metal EDTA salt.

31. The method of claim 30, wherein the density gradient forming agent is an alkali metal EDTA salt.

32. The method of claim 31, wherein the density gradient forming agent is a sodium metal EDTA salt.

33. The method of claim 32, wherein the density gradient forming agent is NaCuEDTA, NaFEDTA, or NaBiEDTA.

* * * * *

UNITED STATES PATENT AND TRADEMARK OFFICE
CERTIFICATE OF CORRECTION

PATENT NO. : 7,320,893 B2  Page 1 of 1
APPLICATION NO. : 10/795237
DATED : January 22, 2008
INVENTOR(S) : Ronald D. MacFarlane et al.

It is certified that error appears in the above-identified patent and that said Letters Patent is hereby corrected as shown below:

Column 16, Claim 5, Line 11: delete "NaCuBDTA" and insert --NaCuEDTA--.

Column 16, Claim 18, Line 46: delete "speotrometry" and insert --spectrometry--.

Column 16, Claim 19, Lines 58-59: delete "non-sedimental" and insert --non-sedimented--.

Column 18, Claim 33, Line 27: delete "NaFEDTA" and insert --NaFeEDTA--.

Signed and Sealed this

Twentieth Day of May, 2008

JON W. DUDAS
*Director of the United States Patent and Trademark Office*